(12) United States Patent
Nervegna et al.

(10) Patent No.: US 9,157,937 B2
(45) Date of Patent: Oct. 13, 2015

(54) CAPACITANCE TO DIGITAL CONVERTER AND METHOD

(71) Applicant: Silicon Laboratories Inc., Austin, TX (US)

(72) Inventors: Louis Nervegna, Andover, MA (US); Bruce Del Signore, Hollis, NH (US)

(73) Assignee: Silicon Laboratories Inc., Austin, TX (US)

( * ) Notice: Subject to any disclaimer, the term of this patent is extended or adjusted under 35 U.S.C. 154(b) by 37 days.

(21) Appl. No.: 13/954,955

(22) Filed: Jul. 30, 2013

(65) Prior Publication Data

US 2014/0375374 A1 Dec. 25, 2014

Related U.S. Application Data

(63) Continuation of application No. 13/925,781, filed on Jun. 24, 2013.

(51) Int. Cl.
*G01N 27/26* (2006.01)
*G01R 17/10* (2006.01)
*G01R 27/26* (2006.01)
*G01D 5/24* (2006.01)

(52) U.S. Cl.
CPC .............. *G01R 17/105* (2013.01); *G01N 27/26* (2013.01); *G01R 27/2605* (2013.01); *G01D 5/24* (2013.01); *Y10T 307/729* (2015.04)

(58) Field of Classification Search
CPC .......................... G01R 27/2605; G01R 17/105

USPC ............. 327/337; 307/86, 125; 324/439, 711, 324/706, 720
See application file for complete search history.

(56) References Cited

U.S. PATENT DOCUMENTS

| | | | |
|---|---|---|---|
| 3,562,641 A * | 2/1971 | Fulks | 324/680 |
| 3,573,816 A * | 4/1971 | Helgeland | 324/706 |
| 3,576,491 A * | 4/1971 | Thornton | 324/711 |
| 7,315,200 B2 | 1/2008 | Holberg et al. | |
| 7,554,134 B2 | 6/2009 | Cummins | |
| 8,007,167 B2 | 8/2011 | Cummins | |
| 8,145,175 B2 | 3/2012 | Miyano et al. | |
| 8,274,327 B2 | 9/2012 | Uchida | |
| 8,357,958 B2 | 1/2013 | Cummins | |
| 8,513,982 B1 | 8/2013 | Garrity et al. | |
| 2007/0241798 A1 | 10/2007 | Masenas | |
| 2008/0094140 A1 | 4/2008 | Lim et al. | |
| 2009/0284285 A1 | 11/2009 | Fagg | |

(Continued)

OTHER PUBLICATIONS

O'Connell I, T. Scanlan "Sigma Delta Analog to Digital Converter for use in a Remote Sensing Application". 2007 IEEJ International Analog VLSI Workshop, Nov. 7-9, 2007, Limerick Ireland.

*Primary Examiner* — Lam T Mai
(74) *Attorney, Agent, or Firm* — Cesari & Reed LLP; R. Michael Reed

(57) ABSTRACT

An integrator circuit includes a switched capacitor bridge including first and second inputs and first and second outputs. The switched capacitor bridge is configured to sample first and second reference voltages twice per unit time interval. The integrator circuit further includes an integrator coupled to the first and second outputs and configured to integrate charge dumped into the first and second outputs twice per unit time interval.

20 Claims, 6 Drawing Sheets

(56) References Cited

U.S. PATENT DOCUMENTS

| | | |
|---|---|---|
| 2010/0201424 A1 | 8/2010 | Miyano et al. |
| 2010/0264751 A1 | 10/2010 | Lida et al. |
| 2010/0327819 A1 | 12/2010 | Macdougall |
| 2011/0215864 A1 | 9/2011 | Uchida |
| 2013/0285705 A1 | 10/2013 | Kabir et al. |
| 2014/0026642 A1 | 1/2014 | OConnell |
| 2014/0026652 A1 | 1/2014 | Cummins et al. |
| 2014/0146572 A1 | 5/2014 | Ye et al. |

* cited by examiner

CAPACITANCE TO DIGITAL CONVERTER AND METHOD

CROSS-REFERENCE TO RELATED APPLICATION(S)

This application is a Continuation of U.S. patent application Ser. No. 13/925,781 filed on Jun. 24, 2013 and entitled "Circuit Including a Switched Capacitor Bridge and Method," which is incorporated herein by reference in its entirety.

FIELD

The present disclosure is generally related to measurement circuits, and more particularly to measurement circuits configured to sense an unknown electrical parameter using a bridge circuit.

BACKGROUND

Capacitance measuring sensors, such as pressure sensors and humidity sensors, can be configured to deliver an electrical signal that can be evaluated in response to very small changes in a measured parameter. Such sensors may be coupled to an evaluation circuit configured to convert the smallest changes in capacitance into an output signal. Due to the small size of the capacitances to be detected, analog amplifiers are sometimes used to scale the analog signal and the amplified analog signal may subsequently be converted from analog to digital.

SUMMARY

In an embodiment, an integrator circuit includes a switched capacitor bridge including first and second inputs and first and second outputs. The switched capacitor bridge is configured to sample first and second reference voltages twice per unit time interval. The integrator circuit further includes an integrator coupled to the first and second outputs and configured to integrate charge dumped into the first and second outputs twice per unit time interval.

In another embodiment, a method of integrating a measured capacitance includes selectively switching first and second inputs and first and second outputs of a capacitive bridge twice per unit time interval. The method further includes integrating charges on the first and second outputs of the capacitive bridge twice per unit time interval to produce an integrated output signal.

In still another embodiment, an integrator circuit includes a switched capacitor bridge including first and second inputs and first and second outputs. The switched capacitor bridge is configured to sample first and second reference voltages twice per unit time interval. The integrator circuit further includes an integrator including first and second integrator inputs coupled to the first and second outputs of the switched capacitor bridge and including first and second integrator outputs. The integrator is configured to sample and integrate charge twice per unit time interval to produce two integrated samples per unit time interval. The integrator circuit further includes a circuit coupled to the first integrator and configured to decimate the two integrated samples per time interval to produce an output signal representing one integrated sample per time unit.

BRIEF DESCRIPTION OF THE DRAWINGS

In the following discussion, the same reference numbers are used in the various embodiments to indicate the same or similar elements.

DETAILED DESCRIPTION OF ILLUSTRATIVE EMBODIMENTS

Embodiments of a switched capacitor bridge are described below that can be used to measure very small changes in capacitance (such as less than 0.01 fF) with both high resolution (such as greater than 16 bits) and low power consumption (such as less than 60 µA). In an example, the switched capacitor bridge can be used to measure changes in capacitance less than 0.01 fF with a resolution greater than 16 bits, while consuming less than 60 µA of current. In an embodiment, a circuit includes a bridge circuit of four capacitors having two inputs configured to be selectively coupled to voltage sources through a first switching network and two outputs configured to be selectively coupled to inputs of an integrator circuit through a second switching network. In an embodiment, switches of the first and second switch networks are selectively activated to sample and integrate charges on both phases of a clock period (i.e. twice per clock period). The switched capacitor bridge can be configured to combine the high accuracy of a resistive-type Wheatstone bridge with the input switching network of a switched capacitor delta-sigma integrator, providing a reduced circuit area and reduced power consumption relative to a circuit configured to implement these circuit functions separately.

In one embodiment, a delta-sigma based capacitance-to-digital converter (CDC) architecture is described that includes the bridge circuit, the integrator circuit, and the switching networks and that can be used in connection with any capacitive-based measurement/instrumentation system to provide both high accuracy and low power consumption. The delta-sigma CDC architecture may be used in applications with a relatively low bandwidth such as on the order of approximately 100 Hz. In an embodiment, the delta-sigma CDC architecture may be used to implement battery-powered humidity sensors, pressure sensors, or other types of sensors. In a particular illustrative example, the delta-sigma CDC architecture may be configured to provide a 16-bit or greater resolution with a least significant bit size of approximately 0.005 fF, while consuming 59 µA and using a circuit area of 220 µm×340 µm in a 0.18 µm process.

The switched capacitor bridge mimics the performance of the resistive Wheatstone bridge, while sensing small changes in capacitance with approximately the same accuracy that a classical resistive Wheatstone bridge senses small changes in resistance. To illustrate the switched capacitor bridge concept, a traditional resistive Wheatstone bridge coupled to the input of a continuous-time integrator is described below with respect to FIG. 1.

Figure 1:
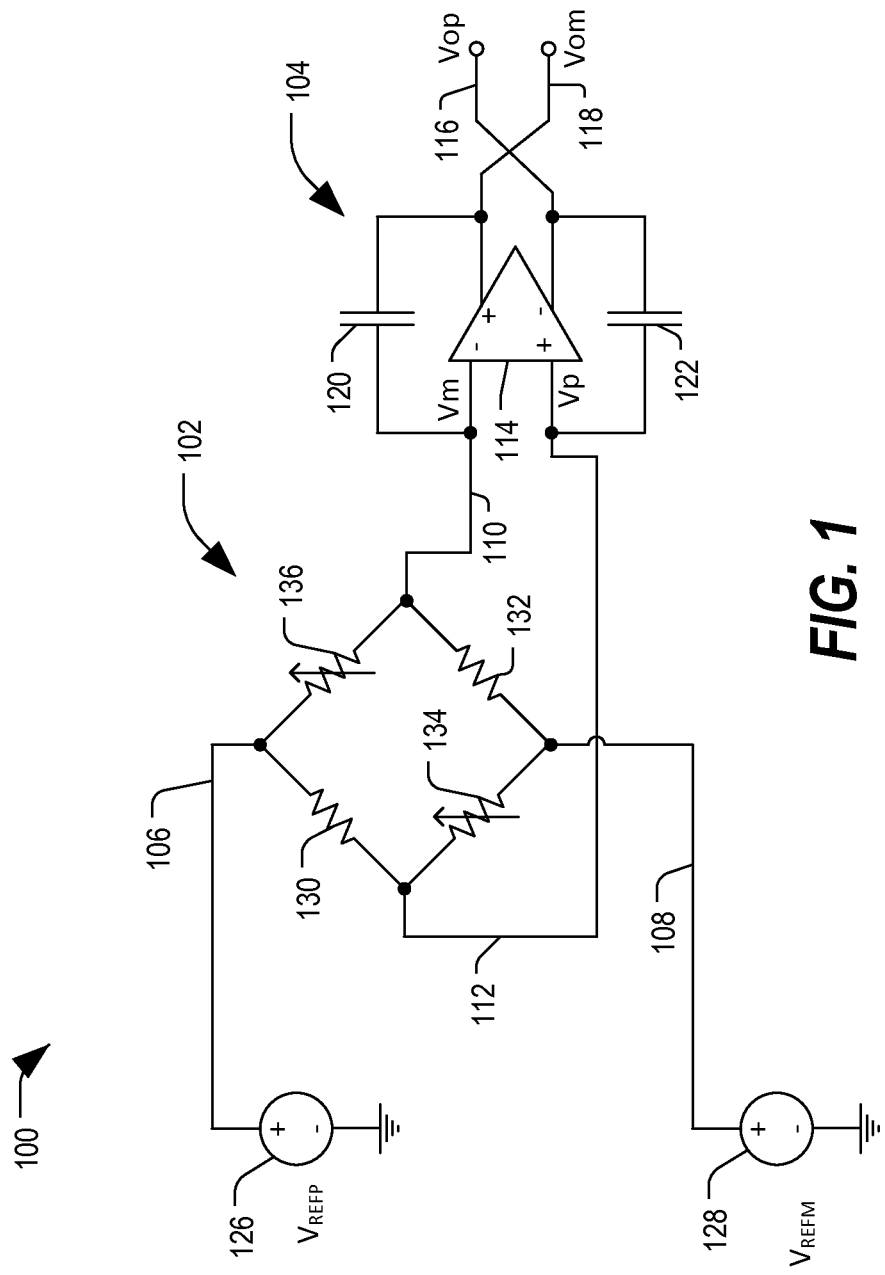
FIG. 1 is a block diagram of a circuit including a conventional Wheatstone bridge coupled to a continuous-time integrator.

FIG. 1 is a block diagram of a circuit 100 including a conventional Wheatstone bridge 102 coupled to a continuous-time integrator 104. Wheatstone bridge 102 includes an input 106 that may be coupled to a first reference voltage source 126 ($V_{REFP}$), which may provide a reference voltage designated as plus (e.g. the supply voltage or the voltage output of a bandgap reference circuit) and includes an input 108 that may be coupled to a second reference voltage source 128 ($V_{REFM}$), which may provide a reference voltage designated as minus (e.g. ground). Wheatstone bridge 102 further includes an output 110 to provide a voltage to a negative (minus) input Vm of integrator 104 and includes a second output 112 to provide a voltage to a positive (plus) input Vp of integrator 104. Wheatstone bridge 102 includes a resistor 130 coupled between input 106 and output 112, a resistor 132 coupled between input 108 and output 110, a variable resistor 134 coupled between input 108 and output 112, and a variable resistor 136 coupled between input 106 and output 110. The resistances of variable resistors 134 and 136 are configured to vary according to a parameter to be sensed, such as temperature, pressure, or other parameters.

Integrator 104 includes a fully differential amplifier 114 including a negative (minus) input terminal Vm coupled to output 110 and a positive (plus) input terminal Vp coupled to output 112. Circuit 100 includes an output 116 to provide a positive (plus) output voltage (Vop) and an output 118 to provide a negative (minus) output voltage (Vom). Differential amplifier 114 further includes a positive output terminal coupled to Vom 118 as well as a negative output terminal coupled to Vop 116. Positive and negative output voltages Vop 116 and Vom 118 are designated as the opposite polarity of the respective output terminal that they couple to on fully differential amplifier 114, which is why the lines are drawn as crisscrossed in FIG. 1. Integrator 104 further includes a capacitor 120 coupled between output 118 and output 110. Additionally, integrator 104 includes a capacitor 122 coupled between output 116 and output 112.

In an embodiment, resistors 130 and 132 may be fixed, and variable resistors 134 and 136 operate as sense resistors to sense small delta changes in resistance. Additionally, the reference voltages ($V_{REFP}$ and $V_{REFM}$) may be constant with time (e.g. DC voltages). The negative feedback in the integrator 104 forces the voltages on outputs 110 and 112 to the same voltage level, such that the difference between voltages (Vp and Vm) is zero, forming a differential virtual ground. The delta conductance (1/resistance) between variable resistors 134 and 136 and resistors 130 and 132 (i.e. $1/R_{134,136}$-$1/R_{130,132}$) may be detected as a differential current into the differential virtual ground node of amplifier 114. This differential current is integrated onto capacitors 120 and 122 according to the following equation which represents the constitutive relation between voltage and current of a capacitor:

$$v = \frac{1}{c}\int i\,dt. \quad (1)$$

The voltage integrated onto capacitors 120 and 122 operates to produce a differential output voltage (Vop–Vom). Application of Kirchhoff's current law (KCL) at the differential virtual ground node (outputs 110 and 112) verifies the integrating behavior of the circuit as described above (assuming zero charge on capacitors 120 and 122 at the outset) according to the following equation:

$$V_{op}(t) - V_{om}(t) = \frac{(V_{refp} - V_{refm})}{C_{120,122}} \int \left(\frac{1}{R_{134,136}(t)} - \frac{1}{R_{130,132}}\right)dt. \quad (2)$$

Equation 2 above assumes that resistors 134 and 136 are approximately matched to one another as represented by their common value $R_{134,136}$, and that resistors 130 and 132 are also approximately matched to one another as represented by their common value $R_{130,132}$. Equation 2 also assumes that capacitors 120 and 122 are approximately matched to one another as represented by their common value $C_{120,122}$. Additionally, assuming that $R_{134,136}(t)$ varies in time sufficiently slowly that it can be considered as a constant, Equation 2 reduces to the following equation:

$$V_{op}(t) - V_{om}(t) = \frac{(V_{refp} - V_{refm})}{C_{120,122}} \int \left(\frac{1}{R_{134,136}} - \frac{1}{R_{130,132}}\right)dt. \quad (3)$$

The offset resistors 130 and 132 are fixed and the sensor resistors 134 and 136 vary. Evaluating the integral in Equation 3, the differential output voltage Vop–Vom can then be shown to be:

$$V_{op}(t) - V_{om}(t) = \frac{\left(\frac{1}{R_{134,136}} - \frac{1}{R_{130,132}}\right)}{C_{120,122}}(V_{refp} - V_{refm})t. \quad (4)$$

In a particular embodiment, variable resistors 134 and 136 may be thermistors, which have a resistance that varies with temperature. Variations in the temperature cause the currents flowing through outputs 110 and 112 to change, which changes can be detected by integrator 104.

In an embodiment described below with respect to FIG. 2, the conventional Wheatstone bridge is replaced by a switched capacitor bridge that may be selectively coupled to an integrator circuit to provide the first integrator of a capacitive-to-digital converter (CDC) architecture, which may include any number of integrators.

Figure 2:
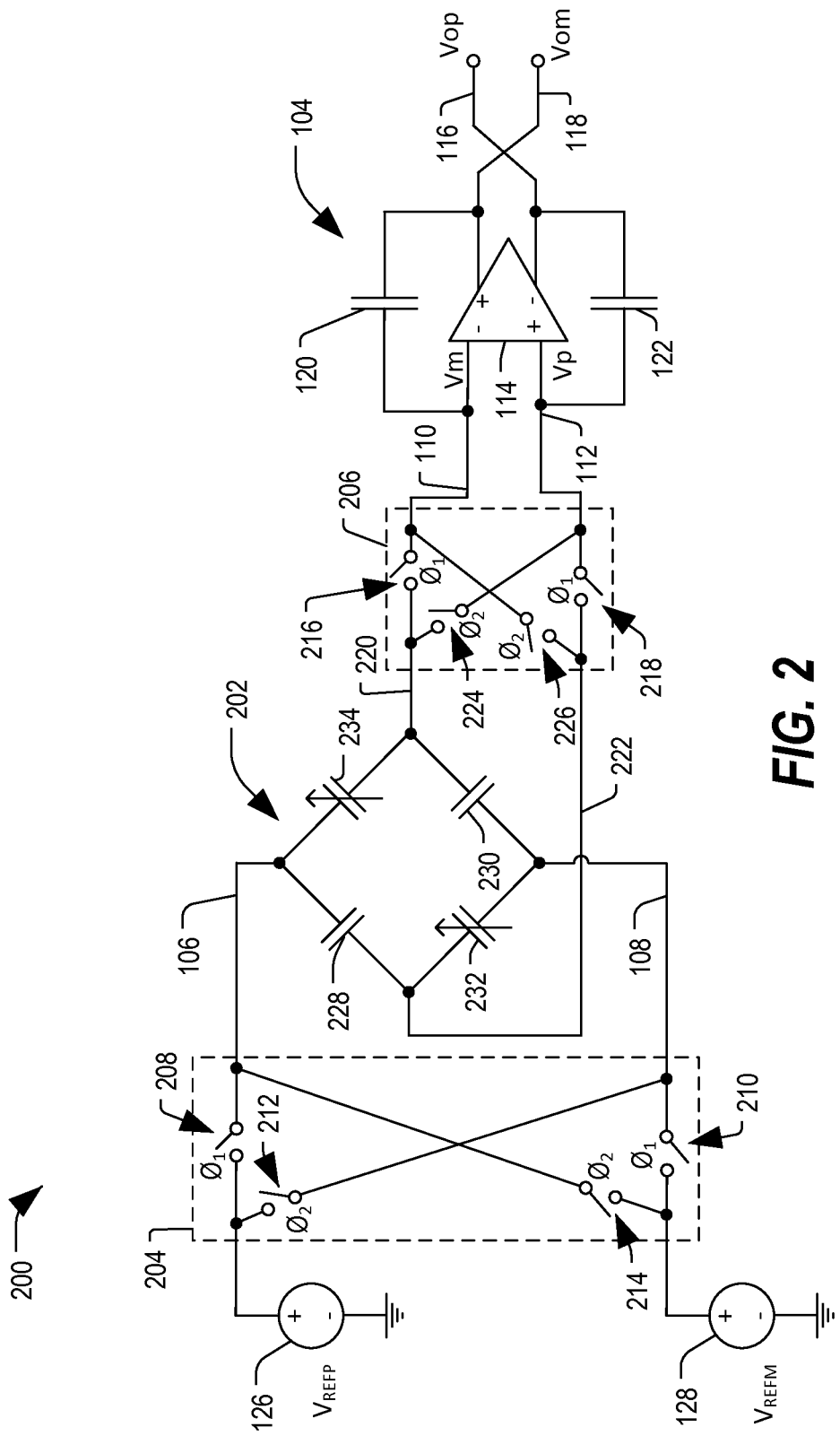
FIG. 2 is a block diagram of a circuit including a switched capacitor bridge coupled to the continuous-time integrator according to an embodiment.

FIG. 2 is a block diagram of a circuit 200 including a switched capacitor bridge 202 configured to be selectively coupled to the continuous-time integrator 104 according to an embodiment. Circuit 200 may function as the first integrator of a delta-sigma modulator (a type of analog-to-digital converter). In this example, the loop filter feedback network of the delta-sigma modulator (which may be switched-capacitor based) is omitted from circuit 200 for simplicity of discussion and will instead be described below with respect to FIG. 4. It should be understood that the loop filter feedback network (not shown in FIG. 2) sets the common mode voltage level at differential virtual ground nodes Vp 112 and Vm 110.

Circuit 200 includes voltage sources 126 and 128 and integrator 104 as described with respect to FIG. 1. Further, circuit 200 includes a switch circuit 204 coupled between voltage sources 126 and 128 and inputs 106 and 108. Circuit 200 further includes a switch circuit 206 coupled between nodes 220 and 222 of capacitor bridge 202 and outputs 110 and 112 coupled to the negative and positive inputs of amplifier 114 of integrator 104.

Capacitor bridge 202 includes a capacitor 228 coupled between input 106 and node 222, and includes a capacitor 230 coupled between input 108 and node 220. Capacitor bridge 202 further includes a variable capacitor 232 coupled between input 108 and node 222, and includes a variable capacitor 234 coupled between input 106 and node 220.

Analogous to Wheatstone bridge 102 in FIG. 1, capacitors 228 and 230 are fixed capacitors, while variable capacitors 232 and 234 operate as sense capacitors that vary with the parameter to be measured (such as humidity). Also analogous to FIG. 1, the reference voltages ($V_{REFP}$ and $V_{REFM}$) may be constant with time (e.g. DC voltages).

Switch circuit 204 includes a switch 208 coupled between voltage source 126 and input 106. Switch circuit 204 further includes a switch 210 coupled between voltage source 128 and input 108. Switch circuit 204 also includes a switch 212 coupled between voltage source 126 and input 108 and includes a switch 214 coupled between voltage source 128 and input 106.

Switch circuit 206 includes a switch 216 coupled between node 220 and an output 110, which is coupled to the negative input of amplifier 114. Switch circuit 206 further includes a switch 218 coupled between node 222 and output 112, which is coupled to the positive input of amplifier 114. Switch circuit 206 includes a switch 224 coupled between node 220 and output 112, and includes a switch 226 coupled between node 222 and output 110.

During a first phase ($\emptyset_1$) of a clock cycle (n), switches 208, 210, 216 and 218 are closed, and switches 212, 214, 224, and 226 are open. The reference voltages $V_{REFP}$ and $V_{REFM}$ are applied to inputs 106 and 108, respectively, of capacitor bridge 202, which provides first output signals to nodes 220 and 222. The charges from $V_{REFP}$ and $V_{REFM}$ are therefore sampled onto capacitors 228, 230, 232, 234 during this first phase via switches 208 and 210. Nodes 220 and 222 are coupled to negative and positive inputs, respectively, of amplifier 114 and to capacitors 120 and 122 of integrator 104. Therefore, charge is also dumped onto integrating capacitors 120 and 122 during this first phase via switches 216 and 218, and the operation of integration is thus performed by circuit 200 during this first phase resulting in an integrated value at voltage outputs 116 and 118 (Vop-Vom).

During a second phase ($\emptyset_2$) of the clock cycle, switches 208, 210, 216, and 218 are opened, and switches 212, 214, 224, and 226 are closed. The reference voltages $V_{REFP}$ and $V_{REFM}$ are applied to inputs 108 and 106, respectively. The charges from $V_{REFP}$ and $V_{REFM}$ are therefore sampled onto capacitors 228, 230, 232, 234 during this second phase via switches 212 and 214. It should be noted that charge is sampled onto bridge 202 on the second phase ($\emptyset_2$) with the opposite polarity as the first phase ($\emptyset_1$). Node 220 is coupled to the positive input of amplifier 114 and to capacitor 122, and node 222 is coupled to the negative input of amplifier 114 and to capacitor 120. Therefore, charge is also dumped onto integrating capacitors 120 and 122 during this second phase ($\emptyset_2$) via switches 226 and 224, and the operation of integration is thus performed by circuit 200 during this second phase ($\emptyset_2$) resulting in an integrated value at voltage outputs 116 and 118 (Vop-Vom). It should be noted that charge is also dumped onto integrating capacitors 120 and 122 on the second phase ($\emptyset_2$) with the opposite polarity as on the first phase ($\emptyset_1$).

As a result of this switching scheme, charge is sampled onto capacitors 228, 230, 232 and 234 on both clock phases ($\emptyset_1$ and $\emptyset_2$) of a clock cycle (so-called double sampling) via switches 208, 210, 212, 214. It should be noted that the polarity with which the voltage sources 126 and 128 are connected to the bridge 202 is reversed on each phase ($\emptyset_1$ and $\emptyset_2$) by the switch network 204. Additionally, as a result of this switching scheme, charge is dumped onto integrating capacitors 120 and 122 on both clock phases via switches 216, 218, 224, 226, i.e. integration is performed on both clock phases. The polarity with which the bridge 202 is connected to integrator 104 is also reversed on each phase by the switch network 206.

On each clock phase, the negative feedback around integrator 104 forces the voltages on outputs 110 and 112 to the same voltage (Vp=Vm), forming a differential virtual ground (Vp-Vm=0). In this case, the delta capacitance between variable capacitors 232 and 234 and fixed capacitors 228 and 230 (i.e. $C_{232,234} - C_{228,230}$) can be detected as a differential charge that is dumped into the differential virtual ground node of amplifier 114 and onto integrating capacitors 120 and 122 on each clock phase to produce the differential output voltage (Vop-Vom). The sampling and integration operations are both performed together on each clock phase, providing two sample and two integration operations during each clock cycle (note that one clock cycle equals two clock phases ($\emptyset_1$ and $\emptyset_2$)). Therefore, the value of Vop-Vom is updated on each clock phase, and thus the value is updated twice per clock cycle. It should be noted that a conventional integrator updates its voltage output only once per clock cycle.

Application of charge conservation principles at the differential virtual ground node (outputs 110 and 112) verifies the integrating behavior of circuit 200. Assuming capacitors 228 and 230 are approximately matched as represented by their common value $C_{228,230}$ and that capacitors 232 and 234 are approximately matched as represented by their common value $C_{232,234}$, and assuming that capacitance $C_{232,234}(t)$ varies so slowly with time that it can be considered constant, the differential charge (Qp-Qm) provided to capacitors 120 and 122 through the differential virtual ground (110 and 112) on each clock phase is determined according to the following equation:

$$Q_p - Q_m = 2[C_{232,234} - C_{228,230}](V_{refp} - V_{refm}). \quad (5)$$

The charge transferred on each clock phase into the differential virtual ground node (110 and 112) is the discrete-time equivalent of the continuous current flow from the resistive Wheatstone bridge 102 into the differential virtual ground node (110 and 112) in FIG. 1. Based on the relationship between voltage and charge stored on a capacitor V=Q/C, the charge transferred on each clock phase is equivalent to a change in output voltage on each clock phase according to the following equation:

$$V_{op} - V_{om} = 2 \frac{C_{232,234} - C_{228,230}}{C_{120,122}} (V_{refp} - V_{refm}). \quad (6)$$

The total output voltage after a number of clock cycles (n), or equivalently after 2n clock phases, can then be determined according to the following equation:

$$V_{op}[n] - V_{om}[n] = 4 \frac{C_{232,234} - C_{228,230}}{C_{120,122}} (V_{refp} - V_{refm}) n. \quad (7)$$

This equation assumes zero charge on capacitors 120 and 122 at the outset. In Equation 7, the variable n can be viewed as the discrete-time equivalent of the continuous-time variable t in Equation 8 below:

$$V_{op}(t) - V_{om}(t) = \frac{\left(\frac{1}{R_{232,234}} - \frac{1}{R_{228,230}}\right)}{C_{120,122}}(V_{refp} - V_{refn})t. \quad (8)$$

Note that Equation 8 above was previously derived for the resistive Wheatstone bridge based integrator circuit 100 in FIG. 1 as Equation 4, and is repeated here for convenience and to illustrate the similarity with Equation 7 derived for the switched capacitor bridge based integrator circuit 200 in FIG. 2.

Since the time (t) is equal to the number of clock cycles (n) times the clock period (T), it must also be true that the time (t) is equal to the number of clock cycles (n) divided by the frequency (f) according to the following equation:

$$t = n * T = \frac{n}{f}. \quad (9)$$

Equation 9 provides a conversion factor between discrete time (n) and continuous time (t) in Equations 7 and 8 above. Comparing Equations 7 and 8 and applying the conversion factor t=n/f from Equation 9, the switched capacitors 228, 230, 232, and 234 in circuit 200 mimic resistances of Wheatstone bridge 102 in circuit 100, such that the resistance of resistors 130 and 132 is related to the capacitance of capacitors 228 and 230 according to the following equation:

$$R_{130,132} = \frac{1}{4C_{228,230}f}, \quad (10)$$

where the parameter f refers to the switching frequency. By the same method, the variable resistance of resistors 134 and 136 of Wheatstone bridge 102 may be related to the variable capacitance of capacitors 232 and 234 according to the following equation:

$$R_{134,136} = \frac{1}{4C_{232,234}f}. \quad (11)$$

Circuit 200 is configured to reject mismatches between capacitors 228 and 230 and between capacitors 232 and 234 using a chopping feature provided by switch circuits 204 and 206. The following example demonstrates this rejection of mismatch. Assuming mismatched capacitors 228 and 230 and mismatched capacitors 232 and 234, the total charge dumped onto integrating capacitors 120 and 122 of integrator 104 after both clock phases of one full clock cycle can be determined according to the following equation:

$$Q_p - Q_m = 2([C_{232} + C_{234}] - [C_{228} + C_{230}])(V_{refp} - V_{refn}). \quad (12)$$

It should be noted that this equation represents the charge after both clock phases of a full clock cycle, whereas Equation 5 represented the charge after only a single phase. Equation 12 demonstrates how circuit 200 rejects differential mismatch in capacitors 232 and 234 and differential mismatch in capacitors 228 and 230. For example, if $C_{232}$ is larger by an amount ($\Delta_1$) and $C_{234}$ is smaller by the same amount ($\Delta_1$), then the sum $C_{232}+C_{234}$ still remains the same, because the amounts ($\Delta_1$) cancel in the summation. Similarly, if $C_{228}$ is larger by an amount ($\Delta_2$) and $C_{230}$ is smaller by the same amount ($\Delta_2$), then the sum $C_{228}+C_{230}$ still remains the same, because the amounts ($\Delta_2$) cancel in the summation. By switching the input and output signals each phase of the clock signal in the manner previously described for circuit 200, the mismatches in capacitance cancel through the chopping (switching) process. With mismatches rejected, the circuit 200 detects the common mode of capacitors 232 and 234 ($C_{232}+C_{234}$) and the common mode of capacitors 228 and 230 ($C_{228}+C_{230}$) as exemplified by Equation 12. However, the circuit 200 rejects the differential mode of capacitors 232 and 234 and the differential mode of capacitors 228 and 230, which is equivalent to saying that the circuit rejects mismatches in these respective capacitances.

The chopping and fully differential nature of circuit 200 also functions to reject the effects of other sources of mismatch that may be present, including (for example) mismatched switch leakage. If the switches are implemented as MOS transistors, then mismatched leakage may be contributed through the parasitic diode junctions of the switches 208, 210, 212, 214, 216, 218, 224, 226 and through the mismatched sub-threshold leakage through their channels when the switches are off. Further, circuit 200 also functions as a parasitic insensitive integrator when capacitor bridge 202 is coupled to integrator 104 through switch networks 204 and 206 as shown in FIG. 2. For example, parasitic capacitances to ground or parasitic capacitances to the power supply are rejected on all nodes of capacitor bridge 202 to which the switch circuits 204 and 206 are coupled, namely nodes 106, 108, 220, 222. Consequently, the explicitly drawn capacitors 228, 230, 232, 234 of the bridge 202 in FIG. 2 are detected by circuit 200 and not the parasitic capacitances (not drawn in FIG. 2) contributed by the switches or other sources.

Figure 3:
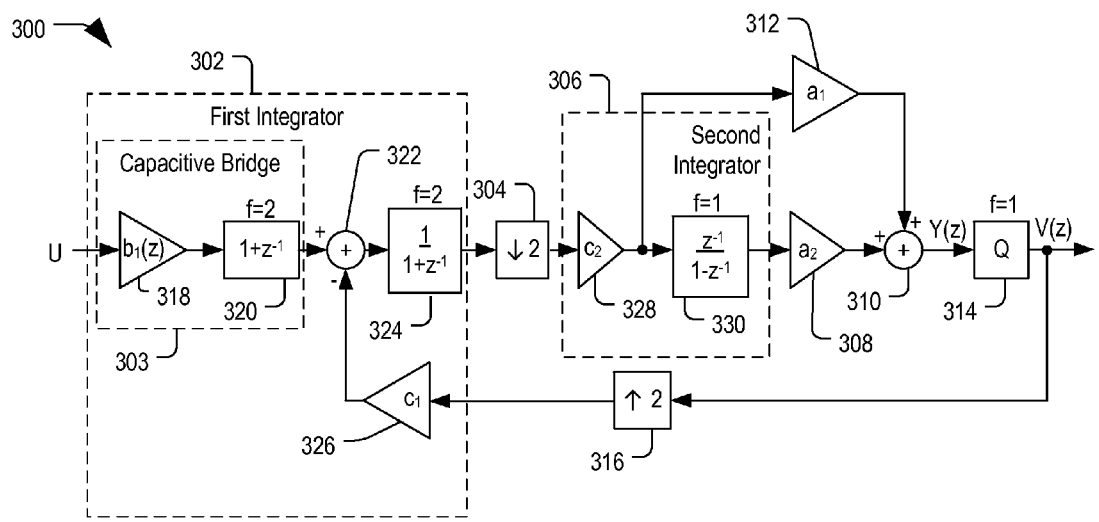
FIG. 3 is a block diagram of a multi-rate delta-sigma modulator including an embodiment of the circuit of FIG. 2.

FIG. 3 is a block diagram of a delta-sigma modulator 300 including an embodiment of the circuit of FIG. 2. Modulator 300 includes a first integrator 302 including an input coupled to a normalized differential reference voltage U and an output coupled to an input of a decimate-by-2 block 304, which has an output coupled to an input of a second integrator 306. Second integrator 306 includes a first output coupled to an input of a scaling block 312 (labeled "$a_1$") and a second output coupled to an input of a scaling block 308 (labeled "$a_2$"). Scaling block 312 has an output coupled to a first input of a summing node 310, which has a second input coupled to an output of scaling block 308, and an output coupled to an input of a quantizer 314 (labeled "Q"). Modulator 300 further includes an interpolate-by-2 block 316 in its feedback path, coupled between the output of quantizer 314 and a feedback input of integrator 302.

First integrator 302 includes capacitive bridge 303 represented by a scaling block 318 (labeled "$b_1$") and a block 320 (labeled "$1+Z^{-1}$") which adds the present sample (represented in the block as "1") to the previous sample (represented in the block as "$Z^{-1}$"), and which has an output coupled to an input of summing node 322. The scaling block 318 includes an input coupled to U and an output coupled to block 320, which has an output coupled to summing node 322. Summing node 322 has a second input coupled to an output of a scaling block 326 (labeled "$c_1$"), which is coupled to the output of interpolate-by-2 block 316. Summing node 322 further includes an output coupled to an input of an delayless integrator 324 (labeled "$1/(1-Z^{-1})$"). Delayless integrator 324 includes an output coupled to the input of decimate-by-2 block 304.

Second integrator 306 includes a scaling block 328 (labeled "$c_2$") including an input coupled to the output of decimation block 304 and an output coupled to an input of a delaying integrator 330 (labeled "$Z^{-1}/(1-Z^{-1})$") and to the input of a scaling block 312. Delaying integrator 330 includes an output coupled to the input of a scaling block 308.

In the illustrated example, first integrator 302 in FIG. 3 is a block diagram model of the circuit 200 in FIG. 2. It should be noted that this model is not intended to represent the exact behavior of circuit 200, but rather to model its most important features. The normalized differential reference voltage U in FIG. 3 is defined as $V_{REFP}-V_{REFM}$ normalized to the differential reference voltage of the modulator. Since the differential reference voltage of the modulator is also chosen as $V_{REFP}-V_{REFM}$ in this embodiment, the value of U is +1 in FIG. 3. The U input to capacitive bridge 303 in FIG. 3 therefore corresponds to reference voltages 126 and 128 in FIG. 2 (assuming they are subtracted differentially and normalized). The capacitive bridge 303 in FIG. 3 corresponds to the collective operation of the switch networks 204 and 206 together with the capacitor bridge 202 in FIG. 2. The summation node 322 in FIG. 3 corresponds to the differential virtual ground 110 and 112 in FIG. 2. The delayless integrator 324 in FIG. 3 corresponds to the integrator 104 in FIG. 2. As mentioned earlier, the circuitry corresponding to the loop filter feedback network of the delta-sigma modulator (corresponding to scaling block 326 inside first integrator 302 of FIG. 3) is omitted from circuit 200 for simplicity of discussion and will instead be described below with respect to FIG. 4.

The capacitive bridge 303 inside first integrator 302 includes a scaling block 318 with a scaling coefficient $b_1(z)$ that varies with the capacitance of variable capacitors 232 and 234 in capacitor bridge 202 of FIG. 2. The normalized differential reference voltage U=+1 at the input to scaling block 318 in FIG. 3 remains constant in this embodiment, and the scaling coefficient $b_1(z)$ varies as the capacitive signal input to the CDC. It should be noted that this behavior is opposite that of a traditional delta-sigma modulated ADC where the voltage typically varies as the signal input and the scaling coefficient $b_1$ remains constant. In this embodiment, the coefficient $b_1(z)$ varies as capacitors 232 and 234 in capacitor bridge 202 according to the following equation:

$$b_1(z) = \frac{C_{232,234}(Z) - C_{228,230}}{C_{120,122}}, \quad (13)$$

where capacitors $C_{232,234}$, $C_{228,230}$, $C_{120,122}$ were previously defined in the description of FIG. 2.

The operation of the block diagram model of the delta sigma modulator in FIG. 3 will now be explained. The constant value of U=+1 is applied to scaling block 318. The output of scaling block 318 is thus equal to $b_1(z)$ as given by Equation 13 (since+1 times $b_1(z)$ is simply equal to $b_1(z)$ itself). Block 320 adds the present sample of $b_1$ (represented by "1" in block 320) to the previous sample of $b_1$ (represented by "$Z^{-1}$" in block 320). The summation node 322 subtracts the feedback signal (as given by the output of scaling block 326) from the present-plus-previous samples of $b_1$ (as given by the output of block 320), and the result of this subtraction (the error signal) is integrated by delayless integrator 324. As expected in a negative feedback system, the feedback signal (output of 326) is subtracted from the forward input path signal (output of 320) as is the case here. Over time, the operation of the negative feedback in the modulator attempts to drive the error signal being integrated (output of 320 minus output of 326) towards zero as the modulator reaches a steady state.

First integrator 302 operates at a normalized frequency of f=2, as labeled in FIG. 3. The reason that first integrator 302 operates at f=2 is because it models circuit 200 in FIG. 2 which integrates on both phases of a single clock cycle, i.e. it integrates twice per clock cycle as opposed to integrating only once per clock cycle (which would instead correspond to a normalized frequency of f=1). As explained earlier, the chopping operation of circuit 200 requires the completion of both clock phases of a single clock cycle in order to properly cancel the differential mismatch in the capacitors of bridge 202. The chopping nature of circuit 200 thus suggests that it is advantageous to only look at the output of circuit 200 (modeled by first integrator 302) once every full clock period after both phases of the clock cycle are complete and the capacitive mismatch has been fully canceled. In the language of Z-domain block diagrams, "looking at the output only once per clock cycle" is equivalent to inserting a decimate-by-2 block 304 after first integrator 302. The mathematical operation of "decimation-by-2" then discards one out-of-every two successive outputs from the first integrator (corresponding to discarding the outputs on one of the two phases) and outputs the remaining one out-of-every two outputs at half the frequency f=1 (corresponding to preserving the outputs on only the opposite phase as the one discarded). Thus the circuitry after the decimate-by-2 block 304 (including second integrator 306 and quantizer 314) operates on the output of the first integrator 302 only once every clock cycle (f=1) as opposed to once every clock phase (f=2).

It should be noted that if the differential amplifier 114 in FIG. 2 were also to be chopped at the same frequency as the capacitive bridge 202 in FIG. 2, then the same benefit of decimating-by-2 would also allow mismatch (offset) in the differential amplifier 114 to fully cancel before being processed by the second integrator 306 and quantizer 314. In this manner, both mismatch in the capacitive bridge 202 and mismatch in the differential amplifier 114 would fully cancel before being processed by the rest of the modulator (second integrator 306 and quantizer 314). The rest of the modulator (second integrator 306 and quantizer 314) therefore only has to process the average of the two chopping phases, which accumulate as a sum at the output of the first integrator (accumulator) 324, instead of having to process each chopping phase separately. To first order, this removes the chopping dynamics from the system, which could otherwise be problematic in a delta sigma modulator. It also simplifies the timing in the design, since the second integrator 306 and quantizer 314 only need to integrate/quantize once per clock cycle as opposed to once per clock phase. Finally, it removes the well-known problem of "path mismatch" present in the feedback paths of fully double-sampled delta sigma modulators (i.e. modulators where all blocks operate at f=2), which is well-known to degrade SNR.

Continuing with the explanation of the operation of FIG. 3, the scaling block 328 scales the output of the decimate-by-2 block 304 by a factor of $c_2$. The output of 328 is then delayed and integrated (at a frequency of f=1) by 330 and then scaled by a factor of $a_2$ by 308. The output of 328 is also fed-forward and scaled by a factor of $a_1$ by 312. The outputs of 312 and 308 are added together by summing node 310 and then quantized (at a frequency of f=1) by 314. The output of the quantizer V(z) represents the 1-bit output of the modulator, whose bit density is proportional to the capacitive input signal $b_1(z)$.

The output of the quantizer V(z) is then fed back to the first integrator. Because the first integrator 302 operates at f=2 and the quantizer 314 operates at f=1, the quantizer output must be subjected to an interpolate-by-2 operation 316 before it can be processed by the first integrator 302. The mathematical operation of "interpolate-by-2" simply inserts a copy of the previous sample in-between the previous and the subsequent sample, such that the interpolated quantizer outputs now appear in pairs at the faster f=2 frequency. For example, if the quantizer produces a "+1" on a particular cycle of the clock, then the result of interpolating-by-2 will be a "+1" on phase 1 ($Ø_1$) of the cycle and a repeated "+1" on phase 2 ($Ø_2$) of the same clock cycle. Similarly, if the quantizer produces a "−1" on a particular cycle of the clock, then the result of interpolating-by-2 will be a "−1" on phase 1 ($Ø_1$) of the cycle and a repeated "−1" on phase 2 ($Ø_2$) of the same clock cycle.

It should be noted that all voltages at all nodes in FIG. 3 are assumed normalized to a differential reference voltage ($V_{REFP} - V_{REFM}$), and that the output of the quantizer is assumed to be equal to either +1 or −1 depending on the value of its normalized input voltage Y(z). With this convention, the input to the capacitive bridge U is equal to $+1 = +(V_{REFP} - V_{REFM})/(V_{REFP} - V_{REFM})$ as previously explained. Also with this convention, there is no need to include a 1-bit DAC in FIG. 3 in the feedback path between the quantizer 314 and first integrator 302 because a +1 input to a 1-bit DAC would produce a normalized output of $+(V_{REFP} - V_{REFM})/(V_{REFP} - V_{REFM}) = +1$ anyway. Similarly, a −1 input to a 1-bit DAC would produce a normalized output of $-(V_{REFP} - V_{REFM})/(V_{REFP} - V_{REFM}) = -1$ anyway. Thus the inclusion of a 1-bit DAC would be mathematically redundant in the block diagram of FIG. 3, and it is omitted for simplicity. It should be noted that these simplifying conventions used in drawing the block diagram in FIG. 3 are for purposes of simplicity and clarity and do not necessarily reflect the exact details of the underlying circuit implementation. The details of the underlying circuit implementation in a particular embodiment will be explained separately below in the context of FIG. 4, FIG. 5, and FIG. 6. These circuit implementations correspond approximately to the block diagram in FIG. 3, as will be explained.

It should be noted that a traditional delta-sigma modulator operates at only one frequency rate. We introduce the terms "multirate modulator" or "multirate loop filter" to describe the new architecture in FIG. 3 which operates at multiple frequency rates (in this particular case, both f=2 and f=1). Traditional delta-sigma loop filters are both linear and time-invariant systems (LTI systems). It should be noted that the operations of decimation and interpolation are only linear operations and are not time-invariant in nature. Therefore, multirate loop filters (such as the embodiment in FIG. 3) are also only linear systems and are not time-invariant, and are therefore not considered LTI systems. The fact that these loop filters are not LTI complicates their closed-form analysis in the frequency domain, particularly the derivation of a single transfer function to describe them.

Figure 4:
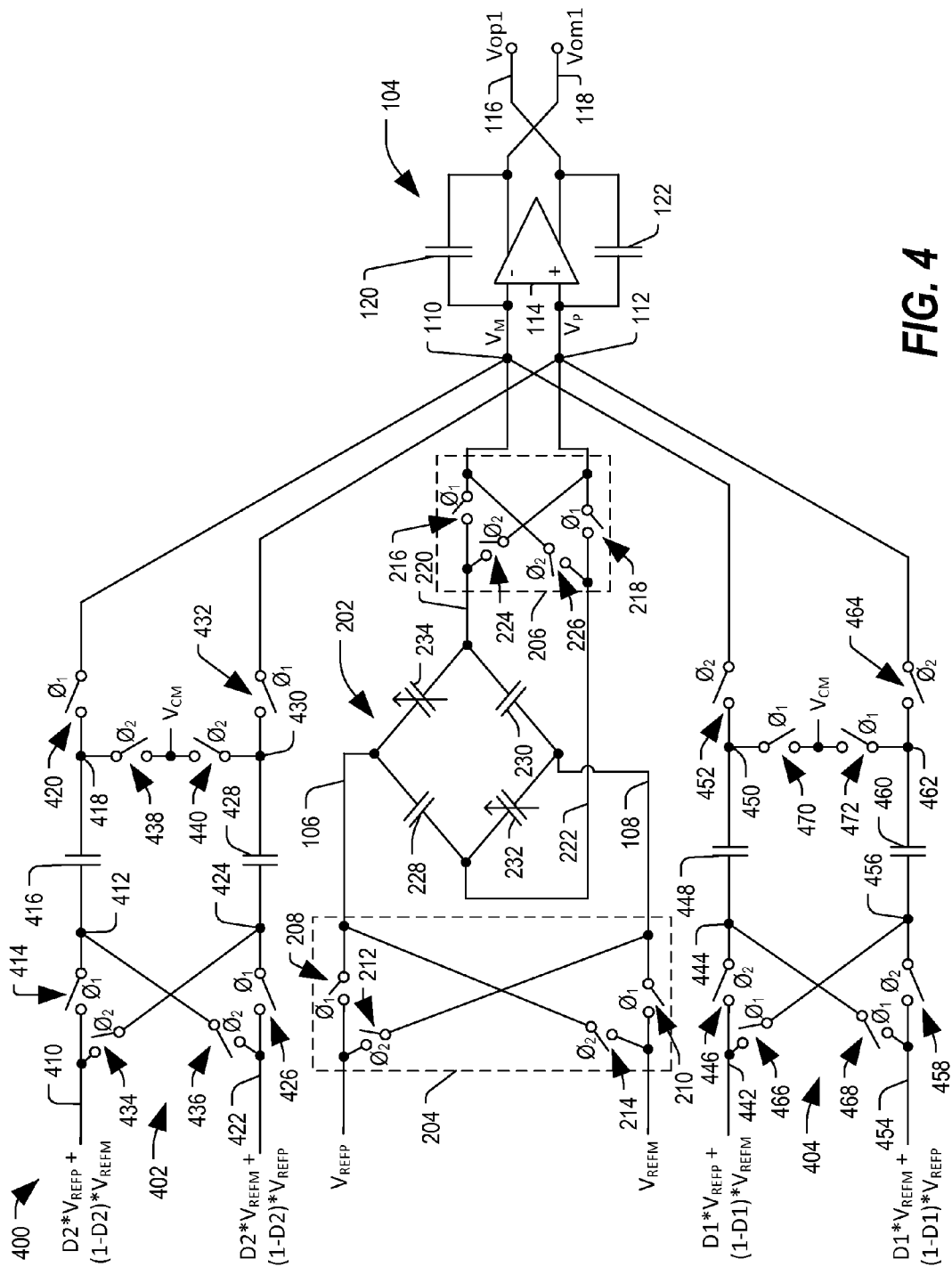
FIG. 4 is a circuit diagram of a first integrator of a capacitance-to-digital converter according to an embodiment.

FIG. 4 is a circuit diagram of a first integrator 400 of a delta-sigma modulated capacitance-to-digital converter according to an embodiment. The topology of the loop filter feedback networks 402 and 404 depicted above and below capacitor bridge 202, respectively, provides a relatively high ratio of feedback signal to feedback noise as will be explained. Circuit 400 corresponds to first integrator 302 in FIG. 3.

First integrator 400 includes all of the elements of FIG. 2, including switch circuits 204 and 206, capacitor bridge circuit 202, and integrator 104. Additionally, first integrator 400 includes a first loop filter feedback network 402 and a second loop filter feedback network 404, which are coupled to nodes 110 and 112 and which were not shown in FIG. 2. The switch circuits 204 and 206 together with the capacitor bridge circuit 202 collectively correspond to blocks 303, 318, 320 in FIG. 3.

The loop filter feedback networks 402 and 404 correspond to the scaling block 326 in FIG. 3. The differential virtual ground nodes 110 and 112 correspond to the summing node 322 in FIG. 3. The integrator 104 corresponds to the delayless integrator block 324 in FIG. 3.

Loop filter feedback network 402 includes a switch 414 coupled between nodes 410 and 412, and includes a capacitor 416 coupled between nodes 412 and 418. Feedback path 402 further includes a switch 420 coupled between nodes 418 and 110. Feedback path 402 also includes a switch 426 coupled between nodes 422 and 424, and includes a capacitor 428 coupled between nodes 424 and 430. Feedback path 402 further includes a switch 432 coupled between nodes 430 and 112. Feedback path 402 also includes a switch 434 coupled between nodes 410 and 424, and a switch 436 coupled between nodes 422 and 412. Feedback path 402 also includes a switch 438 coupled between node 418 and a common mode voltage terminal (labeled "$V_{CM}$"), and includes a switch 440 coupled between nodes 430 and the common mode voltage terminal. In the illustrated example, the common mode voltage $V_{CM}$ may be supplied by an external circuit (acting as a voltage source) not explicitly shown in FIG. 4.

Loop filter feedback path 404 includes a switch 446 coupled between nodes 442 and 444, and includes a capacitor 448 coupled between nodes 444 and 450. Feedback path 404 further includes a switch 452 coupled between nodes 450 and 110. Feedback path 404 also includes a switch 458 coupled between nodes 454 and 456, and includes a capacitor 460 coupled between nodes 456 and 462. Feedback path 404 further includes a switch 464 coupled between nodes 462 and 112. Feedback path 404 also includes a switch 466 coupled between nodes 442 and 456, and a switch 468 coupled between nodes 454 and 444. Feedback path 404 also includes a switch 470 coupled between node 450 and a common mode voltage terminal (labeled "$V_{CM}$"), and includes a switch 472 coupled between nodes 462 and the common mode voltage terminal. In the illustrated example, the common mode voltage $V_{CM}$ is supplied by an external circuit (acting as a voltage source) that is not explicitly shown in FIG. 4.

In a first phase of a clock signal, switches 208, 210, 216, 218 are closed in the forward signal path and switches 212, 214, 224, 226 are open. Further, switches 414, 420, 426, 432 are closed in feedback path 402 and switches 434, 438, 436, 440 are open. Additionally, switches 466, 470, 468, 472 are closed in feedback path 404 and switches 446, 452, 458, 464 are open. In a second phase, switches 208, 210, 216, 218, 414, 420, 426, 432, 466, 470, 468, 472 are open. Further, in the second phase, switches 212, 214, 224, 226 are closed in the forward signal path. Additionally, in the second phase, switches 434, 438, 436, 440, 446, 452, 458, 464 are closed in feedback paths 402 and 404.

The feedback signal at the input to loop filter feedback network 402 is updated by the quantizer/interpolator on every second phase ($Ø_2$) (and is held at the same value by the quantizer/interpolator for the subsequent first phase ($Ø_1$)). This feedback signal at the input to loop filter network 402 is labeled by the equation $D2*V_{REFP} + (1-D2)*V_{REFM}$ at input 410 and is labeled by the equation $D2*V_{REFM} + (1-D2)*V_{REFP}$ at input 422. The variable D2 represents a digital logic value of the quantizer/interpolator, which can be either 1 or 0 depending on the state of the quantizer/interpolator at any given instant of discrete time. The number 2 in the notation D2 is chosen to indicate that the logic value D2 updates on the second phase ($Ø_2$). If the quantizer/interpolator state is such that D2=1, then the differential input (calculated as input 410 minus input 422) to feedback network 402 is equal to $+[V_{REFP} - V_{REFM}]$ according to the labeled equations. If D2=0, then the differential input is equal to $-[V_{REFP}-V_{REFM}]$ according to the labeled equations. It is assumed that a 1-bit DAC (not drawn in FIG. 4) translates the logical value of D2 from the quantizer/interpolator into a differential analog voltage $+[V_{REFP}-V_{REFM}]$ or $-[V_{REFP}-V_{REFM}]$ at the differential inputs 410 and 422 of feedback network 402, according to the equations labeled at 410 and 422.

According to the switching scheme described above, loop filter feedback network 402 samples the updated feedback signal on the second phase ($\emptyset_2$) onto capacitors 416 and 428. On the subsequent first phase ($\emptyset_1$), it again samples the feedback signal (being held at the preceding phase 2 value by the quantizer/interpolator) with opposite polarity as the second phase ($\emptyset_2$) onto capacitors 416 and 428, and simultaneously dumps sampled charge into the differential virtual ground (110 and 112) of integrator 104. Thus, when used in conjunction with integrator 104, feedback network 402 samples the updated value of the feedback signal on the second phase ($\emptyset_2$) and both samples the same feedback signal value (with opposite polarity) and integrates on the first phase ($\emptyset_1$). It should be noted that sampling the same feedback signal with opposite polarity on both clock phases, in the manner just described for network 402, doubles the effective amplitude of the sampled feedback signal while keeping the sampled thermal noise the same as in a standard single-sampled approach. Thus, this technique significantly increases the ratio of feedback signal to feedback noise in network 402.

The feedback signal at the input to loop filter feedback network 404 is updated by the quantizer/interpolator on every first phase ($\emptyset_1$) (and is held at the same value by the quantizer/interpolator for the subsequent second phase ($\emptyset_2$)). This feedback signal at the input to loop filter network 404 is labeled by the equation $D1*V_{REFP}+(1-D1)*V_{REFM}$ at input 442 and is labeled by the equation $D1*V_{REFM}+(1-D1)*V_{REFP}$ at input 454. The variable D1 represents a digital logic value of the quantizer/interpolator, which can be either 1 or 0 depending on the state of the quantizer/interpolator at any given instant of discrete time. The number 1 in the notation D1 is chosen to indicate that the logic value D1 updates on the first phase ($\emptyset_1$). If the quantizer/interpolator state is such that D1=1, then the differential input (calculated as input 442 minus input 454) to feedback network 404 is equal to $+[V_{REFP}-V_{REFM}]$ according to the labeled equations. If D1=0, then the differential input is equal to $-[V_{REFP}-V_{REFM}]$ according to the labeled equations. It is assumed that a 1-bit DAC (not drawn in FIG. 4) translates the logical value of D1 from the quantizer/interpolator into a differential analog voltage $+[V_{REFP}-V_{REFM}]$ or $-[V_{REFP}-V_{REFM}]$ at the differential inputs 442 and 454 of feedback network 404, according to the equations labeled at 442 and 454.

The loop filter feedback network 404 operates in the opposite fashion as that of 402. It samples the updated feedback signal on the first phase ($\emptyset_1$) onto capacitors 448 and 460. On the subsequent second phase ($\emptyset_2$), it again samples the feedback signal (being held at the preceding first phase ($\emptyset_1$) value by the quantizer/interpolator) with opposite polarity as the first phase ($\emptyset_1$) onto capacitors 448 and 460, and simultaneously dumps sampled charge into the differential virtual ground (110 and 112) of integrator 104. Thus, when used in conjunction with integrator 104, feedback network 404 samples the updated value of the feedback signal on the first phase ($\emptyset_1$) and both samples the same feedback signal value (with opposite polarity) and integrates on the second phase ($\emptyset_2$), which is opposite the behavior of network 402. It should again be noted that sampling the same feedback signal with opposite polarity on both phases, in the manner just described for network 404, doubles the effective amplitude of the sampled feedback signal while keeping the sampled thermal noise the same as in a standard single-sampled approach. Thus, this technique significantly increases the ratio of feedback signal to feedback noise in network 404.

The two feedback networks 402 and 404 operate in an "alternating" fashion in circuit 400, such that one network is always integrating on any given phase of the clock cycle (while the other is only sampling). This "alternating" approach ensures that the circuit 400 always integrates a feedback signal, provided by either 402 or 404, whenever it also integrates a capacitive sense signal provide by the forward signal path 204, 202, 206. Since a capacitive sense signal is integrated on both phases of the clock cycle as previously described, the "alternating" feedback network scheme ensures that an appropriate feedback signal is also integrated on each phase of the clock cycle along with the capacitive sense signal.

In this embodiment, the quantizer operates at half the rate of the first integrator, and therefore updates its state only once per clock cycle. Since the quantizer controls the logic values of the previously described variables D1 and D2 in FIG. 4, the logic values of D1 and D2 update only once per clock cycle. It should be noted, however, that even though D1 and D2 are updated only once per clock cycle, they are updated on different phases of the one clock cycle as previously explained. The quantizer updates D1 first on the first phase ($\emptyset_1$) followed by updating D2 on the second phase ($\emptyset_2$). The quantizer then holds the value of D1 on the subsequent second phase ($\emptyset_2$), and holds the value of D2 on the subsequent first phase ($\emptyset_1$). In this embodiment, the quantizer updates D1 and D2 to the same value on the same clock cycle, i.e. the value that D1 is updated to on the first phase ($\emptyset_1$) of the clock cycle is the same as the value that D2 is then subsequently updated to on the second phase ($\emptyset_2$) of the same clock cycle. If the quantizer updates D1 from logic 0 to logic 1 on the first phase ($\emptyset_1$), then the quantizer also updates D2 from logic 0 to logic 1 on the subsequent second phase ($\emptyset_2$). If the quantizer updates D1 from logic 1 to logic 0 on the first phase ($\emptyset_1$), then the quantizer also updates D2 from logic 1 to logic 0 on the subsequent second phase ($\emptyset_2$). If the quantizer updates D1 from logic 1 to logic 1 on the first phase ($\emptyset_1$), then the quantizer also updates D2 from logic 1 to logic 1 on the subsequent second phase ($\emptyset_2$). And finally, if the quantizer updates D1 from logic 0 to logic 0 on the first phase ($\emptyset_1$), then the quantizer also updates D2 from logic 0 to logic 0 on the subsequent second phase ($\emptyset_2$).

It should be noted that the polarity in which the feedback networks 402 and 404 are coupled to the differential virtual ground nodes 110 and 112 is chosen such that the feedback signal provided by 402 or 404 is integrated with a negative sign. It should also be noted that the polarity in which the forward signal path 204, 202, and 206 is coupled to the differential virtual ground nodes 110 and 112 is chosen such that the capacitive sense signal provided by forward path 204, 202, and 206 is integrated with a positive sign. In this manner, the feedback signal is subtracted from the capacitive sense signal on every clock phase, as expected in a negative feedback system.

By applying charge conservation principles to the analysis of circuit 400, the differential voltage at the outputs 116 and 118 (Vop1−Vom1) can be determined in the time domain according to the following two discrete-time difference equations:

$$X_1\left[n-\frac{1}{2}\right] = X_1[n-1] + \left(\frac{C_{232,234}[n-1/2]-C_{228,230}}{C_{120,122}}\right)U + \left(\frac{C_{232,234}[n-1]-C_{228,230}}{C_{120,122}}\right)U - 2\left(\frac{C_{416,428,448,460}}{C_{120,122}}\right)V[n-1], \quad (15)$$

-continued $$X_1[n] = X_1\left[n - \frac{1}{2}\right] + \left(\frac{C_{232,234}[n] - C_{228,230}}{C_{120,122}}\right)U + \left(\frac{C_{232,234}[n-1/2] - C_{228,230}}{C_{120,122}}\right)U - 2\left(\frac{C_{416,428,448,460}}{C_{120,122}}\right)V[n-1]. \quad (16)$$

As will be explained, Equation 15 represents the output of first integrator 400 at the end of phase 2 of the preceding clock cycle (n−1), and Equation 16 represents the output of first integrator 400 at the end of the first phase ($\varnothing_1$) of the current clock cycle (n) (which directly follows the second phase ($\varnothing_2$) of clock cycle n−1). The various variables and parameters used in Equations 15-16 are defined below as:

$$X_1[n] \equiv (V_{op1}[n] - V_{om1}[n])/(V_{refp} - V_{refm}), \quad (17a)$$

$$X_1\left[n - \frac{1}{2}\right] \equiv \left(V_{op1}\left[n-\frac{1}{2}\right] - V_{om1}\left[n-\frac{1}{2}\right]\right)\Big/(V_{refp} - V_{refm}), \quad (17b)$$

$$X_1[n-1] \equiv (V_{op1}[n-1] - V_{om1}[n-1])/(V_{refp} - V_{refm}), \quad (17c)$$

$$U \equiv (V_{refp} - V_{refm})/(V_{refp} - V_{refm}) = 1. \quad (17d)$$

In Equations 15-17, the variable $X_1$ represents the differential output voltage at terminals 116 and 118 (Vop1−Vom1) normalized to the differential reference voltage ($V_{REFP}$−$V_{REFM}$). The parameter U represents the constant differential input voltage coupled to switch network 204 ($V_{REFP}$−$V_{REFM}$) normalized to the differential reference voltage ($V_{REFP}$−$V_{REFM}$). The value of U in Equations 15-17 is therefore equal to +1. The variable V represents the state of the quantizer after being converted to a differential output voltage by a 1-bit DAC (either +[$V_{REFP}$−$V_{REFM}$] or −[$V_{REFP}$−$V_{REFM}$]) normalized to the differential reference voltage ($V_{REFP}$−$V_{REFM}$). The value of V in Equations 15-17 is therefore equal to either +1 or −1, depending on the state of the quantizer at any particular instant of discrete time (n).

The number ½ is used in conjunction with the discrete time variable (n) inside the time index of the difference equations 15-17, e.g., $X_1$[n−½]. Although not mathematically rigorous in the strictest sense, the use of ½ in the time indexing of discrete-time variables is a heuristic notation commonly applied to the difference equations of double-sampled switched capacitor circuits. Assuming that a discrete time duration of 1 represents the passing of one full clock cycle in the difference equations, a discrete time duration of ½ would represent the passing of one half of a clock cycle (i.e. one phase of a clock cycle). For a given switched capacitor circuit, a clock phase can be assigned (in a one-to-one fashion) to the time steps of the discrete-time variable n in the difference equation(s) that model the switched capacitor circuit. To avoid ambiguity, this choice of assignment should be clearly defined for each circuit and variable under discussion. In the first integrator circuit 400 of FIG. 4, the index n is designated as the end of the first phase ($\varnothing$) of the current clock cycle n and the index n−½ is designated as the end of the second phase ($\varnothing_2$) of the preceding clock cycle n−1. Thus, with this choice of assignment, the index n−1 would represent the end of the first phase ($\varnothing_1$) of clock cycle n−1, and the index n+½ would represent the end of the second phase ($\varnothing_2$) of clock cycle n. This assignment/designation extends to any integer choice of n, e.g. n=3 represents the end of the first phase of clock cycle 3 and n=2.5 represents the end of the second phase of clock cycle 2. What follows are three examples to understand this notation and designation: (1) the quantity $X_1$[n−1] in Equations 15-17 represents the value of $X_1$ at the end of the first phase of clock cycle n−1; (2) the quantity $X_1$[n−½] in Equations 15-17 represents the value of $X_1$ at the end of the second phase of clock cycle n−1; and (3) finally, the quantity $X_1$[n] in Equations 15-17 represents the value of $X_1$ at the end of the first phase of clock cycle n.

The terms in Equations 15-16 involving both the differential voltage input U and the variable sense capacitors $C_{232,234}$ are introduced by the circuitry in the forward signal path of circuit 400 consisting of switch networks 204 and 206 and capacitor bridge 202. The parameter U=1 is constant in these terms in Equation 15-16, and the variable sense capacitors minus the fixed offset capacitors ($C_{232,234}$−$C_{228,230}$) represent the true input signal to the ADC, which input signal ultimately gets converted to digital. The terms in Equations 15-16 involving the quantizer output V are introduced by the circuitry in the loop filter feedback paths 402 and 404. The quantizer output is fed back to the first integrator 400 in a negative fashion through switch networks 402 and 404, and thus the signs on the terms in Equations 15-16 involving V are negative. As a result, the terms in the equations involving the quantizer output V are subtracted from the terms involving the capacitive input signal ($C_{232,234}$−$C_{228,230}$), which all have a positive sign. Thus, the feedback is subtracted from the capacitive input signal, resulting in an error difference between the capacitive signal terms and the feedback terms, which error difference is forced toward zero by the normal operation of the delta-sigma modulator, as expected in a negative feedback system. Normal operation of the delta-sigma modulator can be modeled mathematically by iterating through the set of difference equations representing the delta-sigma modulator (including Equations 15-16), while incrementing the value of n on each iteration.

At the end of the second phase ($\varnothing_2$) of clock cycle n−1 as described by Equation 15, the integrator output ($X_1$[n−½]) is a function of both the sense capacitor at the end of the second phase ($\varnothing_2$) of clock cycle n−1 ($C_{232,234}$ [n−½]−$C_{228,230}$) and the sense capacitor at the end of the preceding first phase ($\varnothing_1$) of clock cycle n−1 ($C_{232,234}$ [n−1]−$C_{228,230}$). The integrator output at the end of the second phase ($\varnothing_2$) of clock cycle n−1 ($X_1$[n−½]) is also a function of the integrator output at the end of the preceding first phase ($\varnothing_1$) of clock cycle n−1 ($X_1$[n−1]) and the fed back quantizer output at the end of the preceding first phase ($\varnothing_1$) of clock cycle n−1 (V[n−1]). It should be noted that Equation 15 describes the mathematical operation of "accumulation", i.e. discrete-time integration, as implemented by integrator 400 in FIG. 4 at the end of the second phase ($\varnothing_2$) of the clock cycle n−1. When Equation 15 is explained in terms of its operation as an accumulator, the output at the end of the current second phase ($\varnothing_2$) ($X_1$[n−½]) is the accumulated value of the output at the end of the preceding first phase ($\varnothing_1$) ($X_1$[n−1]), which is itself an accumulated value (such that the equation is recursive), plus a scaled version of the inputs at the end of the current second phase ($\varnothing_2$) ($C_{232,234}$ [n−½]−$C_{228,230}$) and preceding first phase ($\varnothing_1$) ($C_{232,234}$ [n−1]−$C_{228,230}$), plus a scaled version of the feedback at the end of the preceding first phase ($\varnothing_1$) (V[n−1]).

At the end of the first phase ($\varnothing_1$) of clock cycle n as described by Equation 16 (which occurs directly after phase 2 of clock cycle n−1 as described by Equation 15), the integrator output ($X_1$[n]) is a function of both the sense capacitor at the end of the first phase ($\varnothing_1$) of clock cycle n ($C_{232,234}$ [n]−$C_{228,230}$) and the sense capacitor at the end of the preceding second phase ($\varnothing_2$) of clock cycle n−1 ($C_{232,234}$ [n−½]−$C_{228,230}$). The integrator output at the end of the first phase of clock cycle n ($X_1$[n]) is also a function of the integrator output at the end of the preceding second phase of clock cycle n−1 ($X_1[n-\frac{1}{2}]$) and the fed back quantizer output at the end of the preceding first phase of clock cycle n−1 (V[n−1]). Equation 16 again describes the mathematical operation of "accumulation", i.e. discrete-time integration, as implemented by integrator 400 in FIG. 4 at the end of the first phase of the clock cycle n. When Equation 16 is explained in terms of its operation as an accumulator, the output at the end of the current first phase ($X_1[n]$) is the accumulated value of the output at the end of the preceding second phase ($X_1[n-\frac{1}{2}]$), which output is itself an accumulated value (such that the equation is recursive), plus a scaled version of the inputs at the end of the current first phase ($C_{232,234}[n]-C_{228,230}$) and preceding second phase ($C_{232,234}[n-\frac{1}{2}]-C_{228,230}$), plus a scaled version of the feedback at the end of the preceding first phase (V[n−1]).

It should be noted that the feedback signal (V[n−1]) in both Equation 15 and Equation 16 changes only on the first phase and is held constant on the second phase, while the other time-indexed variables in Equations 15-16 change on both the first and second phases (i.e., $X_1[n]$, $X_1[n-\frac{1}{2}]$, $X_1[n-1]$, $C_{232,234}[n]$, $C_{232,234}[n-\frac{1}{2}]$, $C_{232,234}[n-1]$). As previously explained, the feedback signal to network 404 is updated on the first phase and the feedback signal to network 402 is updated to the same value on the subsequent second phase. Assuming that the feedback signal to network 404 is updated on the first phase of clock cycle n−1 (V[n−1]), it must then be true by operation of circuit 400 that this feedback signal (V[n−1]) is integrated on the subsequent second phase of clock cycle n−1. The fact that V[n−1] is integrated on the second phase of clock cycle n−1 is demonstrated by Equation 15 which represents the output of integrator 400 on the second phase of clock cycle n−1. Likewise, assuming that the feedback signal to network 402 is updated on the second phase of clock cycle n−1 to the same value as it was on the preceding first phase of clock cycle n−1 (V[n−1]), it must then be true by operation of circuit 400 that this feedback signal (V[n−1]) is integrated on the subsequent first phase of clock cycle n. The fact that V[n−1] is integrated on the first phase of clock cycle n is demonstrated by Equation 16 which represents the output of integrator 400 on the first phase of clock cycle n. Thus, the same value of the feedback signal (V[n−1]), which updates only on the first phase, is used in both Equation 15 and Equation 16.

Figure 5:
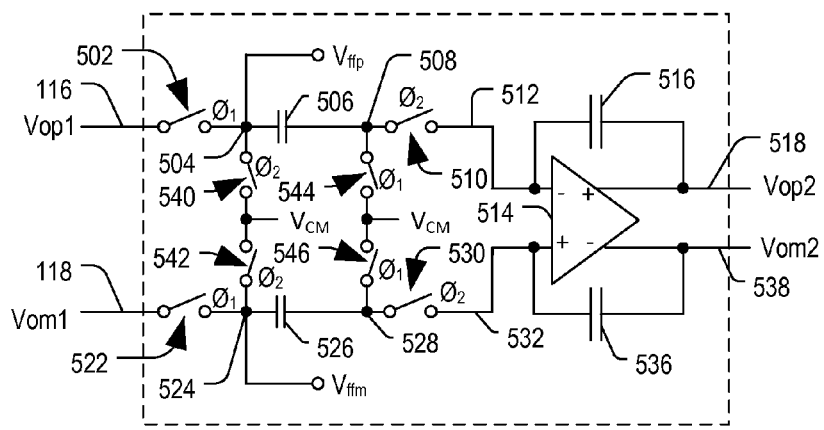
FIG. 5 is a circuit diagram of an embodiment of a second integrator that can be used in conjunction with the first integrator of FIG. 4 as part of a capacitance-to-digital converter (CDC) architecture.

In FIG. 5 below, a possible embodiment of a second integrator of the delta-sigma modulated CDC architecture is described. Further, an example of an implementation of the summation, comparator, and latch circuit is described below with respect to FIG. 6.

FIG. 5 is a circuit diagram of an embodiment of a second integrator 500 that can be used in conjunction with the first integrator 400 of FIG. 4 as part of a delta-sigma modulated CDC architecture. Second integrator 500 includes a switch 502 coupled between output 116 of first integrator 400 and a node 504, which is coupled via capacitor 610 to a node 608 in FIG. 6 (forming a feed-forward path between first and second integrator). A capacitor 506 is coupled between node 504 and a node 508. Second integrator 500 includes a switch 510 coupled between node 508 and a node 512, which is coupled to a negative input of an amplifier 514. Second integrator 500 includes a switch 522 coupled between output 118 of first integrator 400 and a node 524, which is coupled via capacitor 630 to a node 628 in FIG. 6 (forming a feed-forward path between first and second integrator). Second integrator 500 also includes a capacitor 526 coupled between node 524 and a node 528. Second integrator 500 further includes a switch 530 coupled between node 528 and a node 532, which is coupled to a positive input of amplifier 514.

Second integrator 500 further includes a switch 540 coupled between node 504 and a common mode voltage node labeled "$V_{CM}$", and includes a switch 542 coupled between node 524 and the common mode voltage node $V_{CM}$. Second integrator 500 also includes a switch 544 coupled between node 508 and a common mode voltage node $V_{CM}$, and includes a switch 546 coupled between node 528 and common mode voltage node $V_{CM}$. In the illustrated example, the common mode voltage $V_{CM}$ is supplied by an external circuit (acting as a voltage source) not explicitly shown in FIG. 5.

Fully differential amplifier 514 includes a positive output 518 and a negative output 538. Second integrator 500 further includes a capacitor 516 coupled between positive output 518 and node 512. Second integrator 500 also includes a capacitor 536 coupled between negative output 538 and node 532.

The scaling block 328 in FIG. 3 corresponds collectively to switches 502, 510, 522, 530, 540, 542, 544, 546 together with capacitors 506 and 526 in FIG. 5. The integrator 514 in FIG. 5 corresponds to the integrator 330 in FIG. 3. Note that the integrator 514 implements only the delayless portion of the integration $1/(1-Z^{-1})$, and that the delay in the numerator ($Z^{-1}$) of block 320 is actually implemented by the switches 502, 510, 522, 530, 540, 542, 544, 546 together with capacitors 506 and 526 in FIG. 5.

In a first phase corresponding to the first half of the clock cycle, switches 502, 544, 522, and 546 are closed, and switches 540, 542, 510, and 530 are open. The voltage on nodes 116 and 118 is sampled onto capacitors 506 and 526, respectively. During a second phase corresponding to the second half of the clock cycle, switches 502, 544, 522, and 546 are open, and switches 540, 542, 510, and 530 are closed. During this second phase, capacitors 506 and 526 dump charge into the differential virtual ground node (512 and 532) of amplifier 514 and the operation of integration is performed, resulting in an updated output voltage (Vop2−Vom2) at nodes 518 and 538. In summary, circuit 500 samples on the first phase and integrates the sampled voltage on the second phase. It should be noted that the previously determined output voltage (Vop2−Vom2) of integrator circuit 500 is held on the first phase while the switches 502, 544, 522, 546 perform the sampling operation of the input voltage (Vop1−Vom1). The output voltage (Vop2−Vom2) is then updated at the end of the subsequent second phase, after the integration of the sampled voltage has been completed during the second phase.

By applying charge conservation principles to the analysis of circuit 500, the differential voltage at the outputs 518 and 538 (Vop2−Vom2) can be determined in the time domain according to the following discrete-time difference equation:

$$X_2[n] = X_2[n-1] + \left(\frac{C_{506,526}}{C_{516,536}}\right) X_1[n-1]. \quad (18)$$

As will be explained, Equation 18 represents the output of second integrator 500 at the end of the first phase of the current clock cycle n. The various variables used in Equation 18 are defined below as:

$$X_2[n] \equiv (V_{op2}[n]-V_{om2}[n])/(V_{refp}-V_{refm}), \quad (19a)$$

$$X_2[n-1] \equiv (V_{op2}[n-1]-V_{om2}[n-1])/(V_{refp}-V_{refm}), \quad (19b)$$

$$X_1[n-1] \equiv (V_{op1}[n-1]-V_{om1}[n-1])/(V_{refp}-V_{refm}). \quad (19c)$$

In Equations 18 and 19c, the variable $X_1$ represents the differential input voltage at terminals 116 and 118 (Vop1−Vom1) normalized to the differential reference voltage ($V_{REFP}-V_{REFM}$). It should be noted that $X_1$ also represents the differential output voltage at terminals 116 and 118 of first integrator circuit 400 in FIG. 4 (Vop1−Vom1) normalized to the differential reference voltage ($V_{REFP}-V_{REFM}$). In this possible embodiment, terminals 116 and 118 in FIG. 4 are assumed coupled to terminals 116 and 118 in FIG. 5, respectively. Additionally in Equations 18, 19a, and 19b, the variable $X_2$ represents the differential output voltage at terminals 518 and 538 (Vop2−Vom2) normalized to the differential reference voltage ($V_{REFP}-V_{REFM}$). Furthermore, Equation 18 assumes that capacitors 506 and 526 are approximately matched to one another as represented by their common value $C_{506,526}$ and that capacitors 516 and 536 are approximately matched to one another as represented by their common value $C_{516,536}$.

For a given switched capacitor circuit, as previously explained, a clock phase may be assigned (in a one-to-one fashion) to the time steps of the discrete-time variable n in the difference equation(s) that model the switched capacitor circuit. It should be noted that this choice of assignment was already made for variable $X_1[n-1]$ in the context of Equations 15-16 for circuit 400 of FIG. 4. It should be understood that $X_1[n-1]$ represented the value of $X_1$ at the end of the first phase of clock cycle n−1. Since $X_1$ is simply an input to circuit 500, that previous choice of phase assignment for $X_1$ is maintained in Equation 18. To avoid ambiguity, the choice of phase assignment is now also clearly defined for $X_2$ in Equation 18 for integrator circuit 500 of FIG. 5. For variable $X_2$ in circuit 500, the index n is designated as the end of the first phase of the current clock cycle n. Thus, with this choice of assignment, the quantity $X_2[n]$ in Equation 18 represents the value of $X_2$ at the end of the first phase of clock cycle n, and the quantity $X_2[n-1]$ in Equation 18 represents the value of $X_2$ at the end of the first phase of clock cycle n−1. It should be noted here that the clock phase for $X_2$ in Equation 18 for circuit 500 is assigned with the same convention as the clock phase for $X_1$ (and the rest of the time-indexed variables) in Equations 15-16 for circuit 400.

As previously explained, the second integrator 500 samples the output of the first integrator 400 on the first phase, and then integrates this sampled value on the subsequent second phase. While sampling on the first phase, the second integrator 500 also holds its previous output value of $X_2$= [Vop2−Vom2]/[$V_{REFP}-V_{REFM}$] that it determined via integration (accumulation) on the preceding phase 2. Assuming that the second integrator 500 samples the output value of the first integrator 400 on the first phase of clock cycle n−1 ($X_1[n-1]$), it must also be true from the operation of circuit 500 that it integrates this sampled value on the second phase of clock cycle n−1. It must then also be true from operation of circuit 500 that it holds its output value on the subsequent first phase of clock cycle n ($X_2[n]$). The variable $X_2[n]$ in Equation 18 therefore represents this held output value of second integrator 500 on the first phase of clock cycle n, as explained.

Since the second integrator 500 samples the output of the first integrator 400 only on the first phase and ignores the output of the first integrator 400 on the second phase, it implicitly performs the function of the decimate-by-2 block 304 in FIG. 3. Because this is done in an implicit fashion like this, no additional hardware is required to perform the decimation.

Figure 6:
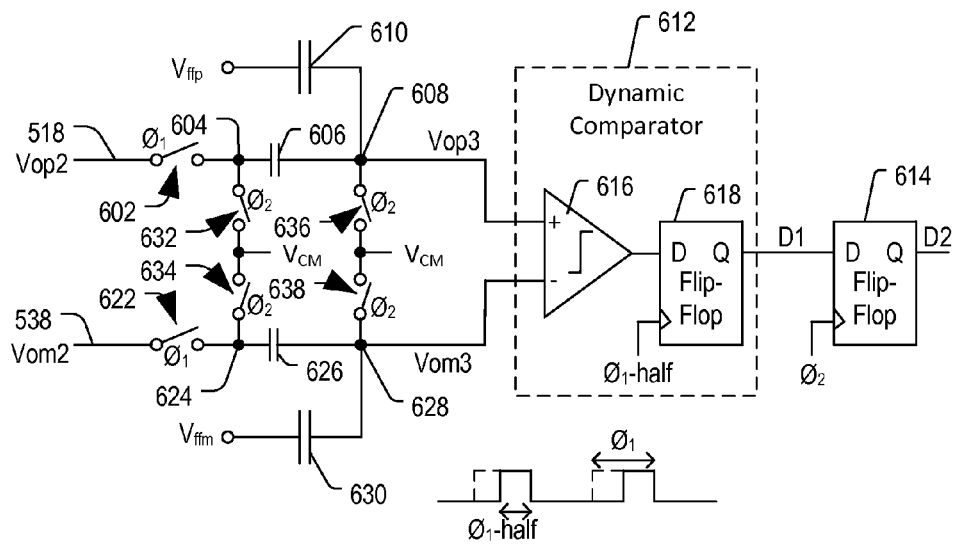
FIG. 6 is a circuit diagram of a summation and comparator/latch circuit according to an embodiment.

FIG. 6 is a circuit diagram of a summation and dynamic comparator circuit 600 according to an embodiment. Circuit 600 performs the three functions of voltage summation, quantization, and interpolation. The summation function of FIG. 6 corresponds collectively to scaling blocks $a_1$ 312 and $a_2$ 308 together with summation node 310 in FIG. 3. The quantization function in FIG. 6 corresponds to block 314 in FIG. 3. And the interpolation function in FIG. 6 corresponds to block 316 in FIG. 3.

Circuit 600 includes a switch 602 coupled between output 518 of amplifier 514 in FIG. 5 and a node 604. Circuit 600 further includes a capacitor 606 coupled between node 604 and a node 608. Circuit 600 also includes a capacitor 610 coupled between node 504 (Vffp) in FIG. 5 and node 608, which is coupled to a positive input of a comparator 616. This capacitor 610 corresponds to the feed-forward path through scaling block 312 in FIG. 3. Circuit 600 includes a switch 622 coupled between output 538 of amplifier 514 in FIG. 5 and a node 624. Circuit 600 further includes a capacitor 626 coupled between node 624 and node 628. Circuit 600 also includes a capacitor 630 coupled between node 524 (Vffm) in FIG. 5 and node 628, which is coupled to a negative input of comparator 616. This capacitor 630 also corresponds to the feed-forward path through scaling block 312 in FIG. 3. Circuit 600 further includes a switch 632 coupled between node 604 and a common mode voltage terminal (labeled "$V_{CM}$"), and includes a switch 634 coupled between the common mode voltage terminal and node 624. Circuit 600 also includes a switch 636 coupled between node 608 and a common mode voltage terminal, and includes a switch 638 coupled between the common mode voltage terminal and node 628. In the illustrated example, the common mode voltage $V_{CM}$ is supplied by an external circuit (acting as a voltage source) not explicitly shown in FIG. 6. The switches 602, 622, 632, 634, 636, 638, 502, 522 and the capacitors 606, 626, 610, 630 collectively function as the portion of circuit 600 which performs the operation of voltage summation, and collectively correspond to scaling blocks $a_1$ 312 and $a_2$ 308 together with summation node 310 in the block diagram of FIG. 3.

Dynamic comparator circuit 612 is modeled by a continuous-time comparator 616 and a D-flip-flop 618. It should be noted that this model of the dynamic comparator (consisting of 616 and 618) is included for simplicity of discussion, and that more power-efficient implementations of the dynamic comparator 612 are preferable (particularly those that possess zero static power), as long as they exhibit the same black-box behavior as the model (616 and 618). The continuous-time comparator 616 in the model includes an output coupled to a D-input of a D-flip-flop 618 in the model, which also has a clock input (indicated by a triangle) configured to receive a timing signal ($\Phi_{1\_half}$), and a Q-output (D1). Circuit 600 further includes a second D-flip-flop 614 including a D-input coupled to the Q-output (D1) of the first D-flip-flop 618. Second D-flip-flop 614 also includes a clock input (indicated by a triangle) configured to receive a timing signal ($\Phi_2$), and includes a Q-output (D2). The dynamic comparator 612 (modeled by continuous-time comparator 616 and D-flip-flop 618) performs the operation of quantization, and corresponds to the quantizer block 314 in the block diagram of FIG. 3. The D-flip-flop 614, together with its input D1 and output D2, performs the operation of interpolation and corresponds to the interpolator block 316 in the block diagram of FIG. 3.

The continuous-time comparator 616 operates by producing a logic value of 1 at its output whenever its inputs are such that Vop3≥Vom3, and by producing a logic value of 0 at its output whenever its inputs are such that Vop3<Vom3. The D-flip-flop, either 618 or 614, operates by changing the logical value of its Q-output to the same logical value as its D-input on every rising edge of its timing signal; the D-flip-flop then holds the value of its Q-output constant (irrespective of the value of its D-input) until the next rising edge of its timing signal. The timing signal $\Phi_2$ is a clock signal that is high on phase 2 and low on phase 1, where phase 1 and phase 2 correspond to the first and second phases of the clock cycle associated with all of the switches in FIG. 2, FIG. 4, FIG. 5, and FIG. 6, as previously explained in the text describing each of those figures. The timing signal $\Phi_1$ is a clock signal that is high on phase 1 and low on phase 2. Finally, the timing signal $\Phi_{1\_}$half is a clock signal that is high on the second-half of phase 1, and low on the first-half of phase 1 and low on all of phase 2. A diagram of the timing signals $\Phi_1$ (dashed line) and $\Phi_{1\_}$half (solid line) is shown at the bottom on FIG. 6.

The outputs D1 and D2 in FIG. 6 represent logic states of the quantizer/interpolator, as previously explained in the context of the first integrator 400 in FIG. 4. The D1 output in circuit 600 of FIG. 6 generates the D1 variable used in the equations labeled at inputs 442 and 454 of circuit 400 in FIG. 4. The D2 output in circuit 600 of FIG. 6 generates the D2 variable used in the equations labeled at inputs 410 and 422 of circuit 400 in FIG. 4. As explained previously, it is assumed that a 1-bit DAC (not drawn in either FIG. 6 or FIG. 4) translates the logical value of D1 from the quantizer/interpolator 612, 616, 618, 614 in FIG. 6 into a differential analog voltage +[$V_{REFP}$-$V_{REFM}$] or -[$V_{REFP}$-$V_{REFM}$] at the differential inputs 442 and 454 of feedback network 404 in FIG. 4, according to the equations labeled at inputs 442 and 454 in FIG. 4. As also explained previously, it is assumed that another 1-bit DAC (also not drawn in either FIG. 6 or FIG. 4) translates the logical value of D2 from the quantizer/interpolator 612, 616, 618, 614 in FIG. 6 into a differential analog voltage +[$V_{REFP}$-$V_{REFM}$] or -[$V_{REFP}$-$V_{REFM}$] at the differential inputs 410 and 422 of feedback network 402 in FIG. 4, according to the equations labeled at inputs 410 and 422 in FIG. 4.

It should be noted that the quantizer (dynamic comparator 612) only updates its output value D1 once per clock cycle on every phase 1 (on the rising clock edge of its timing signal $\Phi_{1\_}$half). By generating the additional output signal D2, the D-flip-flop 614 can be thought of as inserting additional replica updates of D1 on every phase 2 (on the rising clock edge of its timing signal $\Phi_2$). This insertion (or padding) of additional replica quantizer values in-between the original D1 values from quantizer 612 is, by definition, the act of interpolation. The D2 value which is inserted (or padded) in-between each D1 value is simply a replica of the preceding D1 value.

During a first phase of a clock cycle, switches 602 and 622 are closed to couple the differential voltage output (Vop2-Vom2) of second integrator 500 in FIG. 5 to the dynamic comparator circuit 612. Additionally, switches 502 and 522 are closed in the second integrator 500 in FIG. 5 to couple the differential voltage output (Vop1-Vom1) of first integrator 400 in FIG. 4 to the dynamic comparator circuit 612. Additionally, during this first phase, switches 632, 634, 636, 638, 540, 542 are left open. The second integrator output voltage (Vop2-Vom2) is sampled onto capacitors 606 and 626 via switches 602 and 622, and the first integrator output voltage (Vop1-Vom1) is sampled onto capacitors 610 and 630 via switches 502 and 522. With switches 602, 622, 502, 522 closed and switches 632, 634, 636, 638, 540, 542 open, the capacitor network operates in the fashion of a capacitive divider. This capacitive network adds a scaled version of Vop1-Vom1 to a scaled version of Vop2-Vom2 to produce the output voltage Vop3-Vom3 at the differential input (608 and 628) to comparator 616, where the scalings are controlled by the ratio of the common value of capacitors 610 and 630 to the common value of capacitors 606 and 626 (according to the capacitive division that occurs). The comparator block 616 then compares the value of Vop3 at its positive input to the value of Vom3 at its negative input, resulting in either a logic 1 or logic 0 being generated at its output. Half-way through this first phase, on the rising edge of its timing signal $\Phi_{1\_}$half, the D-flip-flop 618 sets its Q-output equal to the comparator output at this instant of time. It should be noted that both the summation portion of circuit 600 and the comparator 616 are designed to be fast enough that the result of the summation and comparison is complete by half-way through this first phase, so that the D-flip-flop 618 records and holds the correct value at its Q-output. The value of the quantizer/interpolator logical state D1, which is generated by the output of the D-flip-flop 618, therefore updates half-way through this first phase to the logical result produced by the comparator. The D-flip-flop 618 then holds this updated value of D1 for a full clock cycle, until the half-way point of the subsequent first phase.

During a second phase of the clock cycle, switches 602, 622, 502, 522 are opened. Furthermore, switches 632, 634, 636, 638, 540, 542 are closed to clear capacitors 606, 626, 610, 630 of all sampled charge. At the beginning of this second phase, on the rising clock edge of timing signal $\Phi_2$, D-flip-flop 614 sets its Q-output value of D2 equal to its D-input value of D1. The value of the quantizer/interpolator logical state D2 therefore updates at the beginning of this second phase and is held for a full clock cycle by D-flip-flop 614 until the beginning of the subsequent second phase.

By applying charge conservation principles to the analysis of circuit 600, the differential voltage at the output of the summation portion of the circuit at nodes 608 and 628 (Vop3-Vom3) can be determined in the time domain according to the following discrete-time difference equation:

$$Y[n] = \left(\frac{C_{610,630}}{C_{610,630}+C_{606,626}}\right)X_1[n] + \left(\frac{C_{606,626}}{C_{610,630}+C_{606,626}}\right)X_2[n]. \quad (20)$$

As will be explained, Equation 20 represents the output of the voltage summation portion of circuit 600 at the end of phase 1 of the current clock cycle n. The various variables used in Equation 20 are defined below as:

$$X_1[n] \equiv (V_{op1}[n]-V_{om1}[n])/(V_{refp}-V_{refm}), \quad (21a)$$

$$X_2[n] \equiv (V_{op2}[n]-V_{om2}[n])/(V_{refp}-V_{refm}), \quad (21b)$$

$$Y[n] \equiv (V_{op3}[n]-V_{om3}[n])/(V_{refp}-V_{refm}). \quad (21c)$$

In Equations 20 and 21a, the variable $X_1$ represents the differential output voltage at terminals 116 and 118 (Vop1-Vom1) of first integrator circuit 400 in FIG. 4 normalized to the differential reference voltage ($V_{REFP}$-$V_{REFM}$). Additionally in Equations 20 and 21b, the variable $X_2$ represents the differential output voltage at terminals 518 and 538 (Vop2-Vom2) of second integrator circuit 500 in FIG. 5 normalized to the differential reference voltage ($V_{REFP}$-$V_{REFM}$). Additionally, in Equations 20 and 21c, the variable Y represents the differential output voltage of the summation portion of circuit 600 (Vop3-Vom3) normalized to the differential reference voltage ($V_{REFP}$-$V_{REFM}$). Furthermore, Equation 20 assumes that capacitors 610 and 630 are approximately matched to one another as represented by their common value $C_{610,630}$, and assumes that capacitors 606 and 626 are approximately matched to one another as represented by their common value $C_{606,626}$.

For a given switched capacitor circuit, as previously explained, a clock phase may be assigned (in a one-to-one fashion) to the time steps of the discrete-time variable n in the difference equation(s) that model the switched capacitor circuit. It should be noted that this choice of assignment was already made for variable $X_1[n]$ in the context of Equations 15-16 for circuit 400 of FIG. 4, and was already made for variable $X_2[n]$ in the context of Equation 18 for circuit 500 of FIG. 5. Recall that $X_1[n]$ represented the value of $X_1$ at the end of the first phase of clock cycle n, and that $X_2[n]$ represented the value of $X_2$ at the end of the first phase of clock cycle n. Since $X_1$ and $X_2$ are simply inputs to circuit 600, those previous choice of phase assignment for $X_1$ and $X_2$ are maintained in Equation 20. To avoid ambiguity, the choice of phase assignment is now also clearly defined for Y in Equation 20 for the summation portion of circuit 600 of FIG. 6. For variable Y in circuit 600, the index n is also designated as the end of the first phase of the current clock cycle n. Thus, with this choice of assignment, the quantity Y[n] in Equation 18 represents the value of Y at the end of the first phase of clock cycle n. It should be noted here that the clock phase for Y in Equation 20 for circuit 600 is assigned with the same convention as the clock phase for $X_1$ (and the rest of the time-indexed variables) in Equations 15-16 for circuit 400 and with the same convention as the clock phase for $X_2$ in Equations 18 for circuit 500. It should also be noted that, even though the summation is complete by the half-way point of the first phase, the assignment is chosen as the end of the first phase for purposes of simplicity and consistency.

It can be seen from Equation 20 that the voltage output of the summation portion of circuit 600 at the end of the first phase (Y[n]) is a weighted sum of the voltage outputs of first integrator 400 ($X_1[n]$) and second integrator 500 ($X_2[n]$) at the end of the first phase, where the weightings are determined by the ratios of capacitors in the summation circuit. These weightings represent the result of capacitive divisions in circuit 600.

The logical value at the output of the quantizer 612 (D1), after conversion to an analog voltage by a 1-bit DAC, can be modeled in the time domain according to the following discrete-time difference equation:

$$V[n]=\text{sgn}(Y[n]). \tag{22}$$

As will be explained, Equation 22 represents the differential output voltage of the 1-bit DAC at the end of the first phase of clock cycle n, after converting the logical value of D1 to either $+[V_{REFP}-V_{REFM}]$ for logic 1 or $-[V_{REFP}-V_{REFM}]$ for logic 0. The various variables used in Equation 22 are defined below as:

$$V[n] \equiv (V_{DACp}[n]-V_{DACm}[n])/(V_{refp}-V_{refm}), \tag{23a}$$

$$Y[n] \equiv (V_{op3}[n]-V_{om3}[n])/(V_{refp}-V_{refm}). \tag{23b}$$

The function sgn(x) is a standard mathematical function defined to be equal to +1 when x≥0, and to be equal to −1 when x<0. In Equations 22 and 23a, the variable V represents the differential output voltage of the 1-bit DAC ($V_{DACp}-V_{DACm}$) normalized to the differential reference voltage ($V_{REFP}-V_{REFM}$). Since $V_{DACp}-V_{DACm}$ is equal to $+[V_{REFP}-V_{REFM}]$ when D1=1 and $-[V_{REFP}-V_{REFM}]$ when D1=0, it must be true that V=+1 when D1=1 and V=−1 when D1=0. In Equations 22 and 23b, the variable Y again represents the differential output voltage of the summation portion of circuit 600 (Vop3−Vom3) normalized to the differential reference voltage ($V_{REFP}-V_{REFM}$).

To avoid ambiguity, the choice of phase assignment is now also clearly defined for variable V in Equation 22 for the quantizer portion of circuit 600 of FIG. 6. For variable V in circuit 600, the index n is also designated as the end of the first phase of the current clock cycle n. Thus, with this choice of assignment, the quantity V[n] in Equation 22 represents the value of V at the end of the first phase of clock cycle n. It should be noted that, even though the quantization is complete by the half-way point of the first phase, the assignment is chosen as the end of the first phase for purposes of simplicity and consistency.

It should be noted that the reason that the quantization needs to complete (and that D1 needs to be updated) by the half-way point of the first phase is because it still allows loop filter feedback network 404 in FIG. 4 a half phase to sample the analog values of $D1*V_{REFP}-(1-D1)*V_{REFM}$ and $D1*V_{REFM}+(1-D1)*V_{REFP}$ provided at its inputs 442 and 454, respectively, on phase 1 in FIG. 4. Without this extra half phase, there would not be sufficient time left over on the first phase for a 1-bit DAC to convert the logical value of D1 to the aforementioned analog values and there would not be enough time to accurately sample these aforementioned analog values onto capacitors 448 and 460 via switches 466, 468, 470, 472 on phase 1.

When the summation and comparator/latch circuit 600 is properly coupled with first integrator circuit 400 and second integrator circuit 500 and with the two aforementioned 1-bit DAC's, as previously described, such that the circuit collectively functions as a delta-sigma modulator, the outputs D1 and D2 provide a digital bit stream having a one's density proportional to:

$$\frac{C_{232,234} - C_{228,230}}{C_{416,428,448,460}}, \tag{24}$$

where $C_{232,234}$ represents the common value of the sensor capacitors 232, 234, and $C_{228,230}$ represents the common value of the offset capacitors 228, 230, and $C_{416,428,448,460}$ represents the common value of the loop filter feedback capacitors 416, 428, 448, 460.

In addition to generating loop filter feedback signals for the first integrator 400, the outputs D1 and D2 provide the 1-bit digital output of the delta-sigma modulated CDC. In this particular embodiment, D2 is chosen as the output of the CDC, but either D1 or D2 may be chosen as the output depending on whether the output is desired to change on the first phase of the clock cycle or the second phase. Either D1 or D2 may be fed into the input of a standard decimation filter (not shown), which provides anti-aliasing filtering and decimation, and which translates the 1-bit digital bit stream into a multi-bit digital word. It should be noted that the decimation filter is not shown in any of the figures.

It should be noted that Equations 15-16, 18, 20, 22 comprise the full set of difference equations which model the delta-sigma modulated CDC architecture in this embodiment. Normal operation of the delta-sigma modulator can be modeled mathematically by iterating through this full set of difference equations representing the delta-sigma modulator (Equations 15-16, 18, 20, 22), while incrementing the value of n on each iteration. This set of difference equations also correspond to the block diagram in FIG. 3, where the block diagram can be viewed as the equivalent frequency-domain representation of the time-domain difference equations 15-16, 18, 20, 22. The scaling coefficients in FIG. 3 correspond one-to-one with ratios of capacitances in the difference equations 15-16, 18, 20, 22, where the one-to-one correspondence can be made by inspection by one skilled in the art.

While the above-discussions were directed to circuit components and their operation, including and relative to a switched capacitor bridge, the method may be performed using various circuit structures. One possible example of a method of operating a switched capacitor bridge is described below with respect to FIG. 7.

Figure 7:
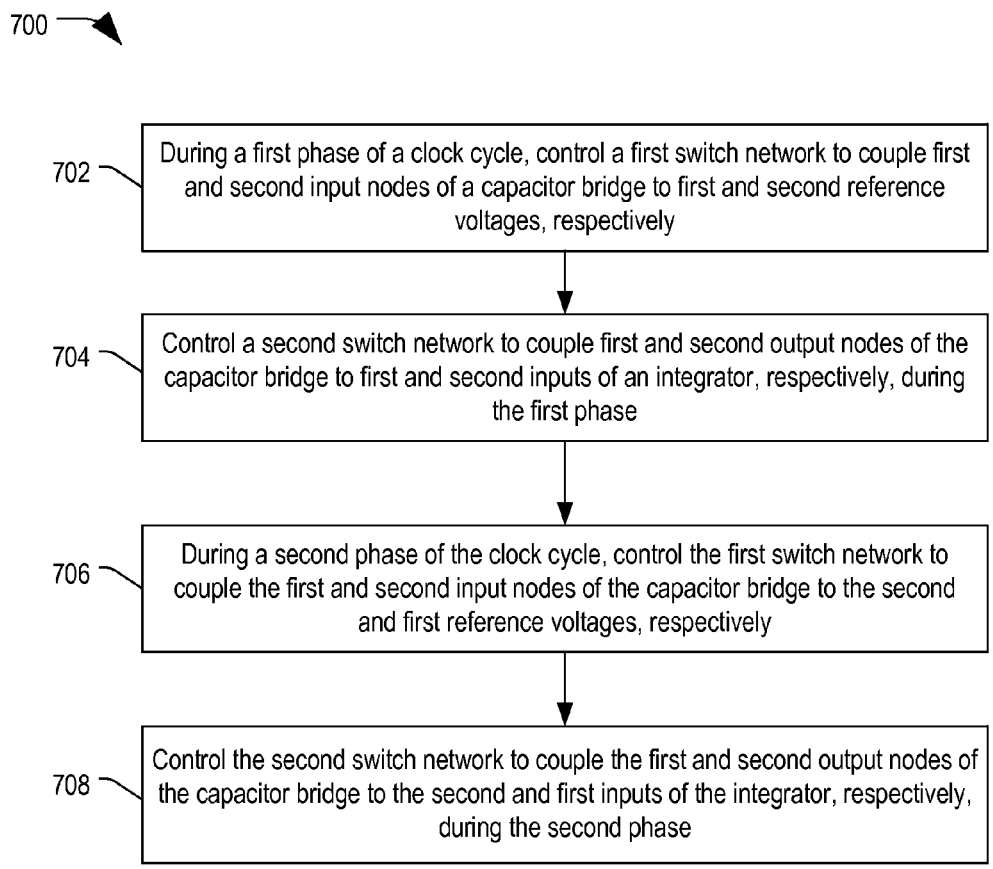
FIG. 7 is a flow diagram of a method of operating a switched capacitor bridge according to an embodiment.

FIG. 7 is a flow diagram of a method 700 of operating a switched capacitor bridge according to an embodiment. At 702, during a first phase of a clock cycle, a first switch network is controlled to couple first and second input nodes of a capacitor bridge to first and second reference voltages, respectively. Advancing to 704, a second switch network is controlled to couple first and second output nodes of the capacitor bridge to first and second inputs of an integrator, respectively, during the first phase. During this first phase, voltages at the first and second inputs are sampled onto the capacitor bridge and the charges are also dumped into the inputs of the integrator.

Moving to 706, during a second phase of the clock cycle, the first switch network is controlled to couple the first and second input nodes of the capacitor bridge to the second and first reference voltages, respectively. Proceeding to 708, the second switch network is controlled to couple the first and second output nodes of the capacitor bridge to the second and first inputs of the integrator, respectively, during the second phase. During the second phase, the voltages at the second and first reference voltages are sampled onto the capacitor bridge and the charges are dumped into the second and first inputs of the integrator, respectively. The method 700 is repeated during a next clock cycle.

In operation, the switching networks operate to switch the input voltages at the input nodes of the capacitor bridge and to switch the output nodes of the capacitor bridge on alternate phases of each clock cycle, sampling and dumping charges on each phase of each clock cycle. When the switches swap the input signals supplied to the capacitor bridge and swap the output signals provided to the integrator, mismatch errors cancel.

In an embodiment, the first integrator may be operated at a first rate, and the second integrator and quantizer may be operated at a second rate that is slower than the first rate. In an example, the first integrator may sample and integrate the change in capacitance twice per clock cycle, while the second integrator may sample and integrate the output signal from the first integrator only once per clock period and the quantizer may quantize only once per clock period.

In conjunction with the circuits, systems, and methods described above with respect to FIGS. 2-7, an integrator circuit is described that includes a switched capacitor bridge 202 configured to sense a physical quantity represented by small changes in capacitance. The integrator circuit further includes a first switch network configured to selectively couple first and second inputs to first and second input nodes of the capacitor bridge, respectively, and includes a second switch network configured to selectively couple first and second output nodes of the capacitor bridge to first and second inputs of an integrator, respectively. During a first phase of a clock period, the first switching network selectively couples the first input to the first input node and the second input to the second input node, and the second switching network selectively couples the first output node to the first input of the integrator and the second output node to the second input of the integrator. During a second phase of the clock period, the first switching network selectively couples the first input to the second input node and the second input to the first input node, and the second switching network selectively couples the first output node to the second input of the integrator and the second output node to the first input of the integrator.

Although the present invention has been described with reference to preferred embodiments, workers skilled in the art will recognize that changes may be made in form and detail without departing from the scope of the invention.

What is claimed is:

1. An integrator circuit comprising:
a switched capacitor bridge including first and second inputs and first and second outputs, the switched capacitor bridge configured to sample first and second reference voltages twice per unit time interval; and
an integrator coupled to the first and second outputs and configured to integrate charge dumped into the first and second outputs twice per unit time interval.

2. The integrator circuit of claim 1, wherein the integrator is configured to integrate charge per unit time dumped into the first and second outputs of the switched capacitor bridge.

3. The integrator circuit of claim 1, wherein the integrator is configured to integrate capacitance of the switched capacitor bridge.

4. The integrator circuit of claim 1, wherein the integrator comprises:
a fully differential amplifier including first and second amplifier inputs coupled to the first and second outputs of the switched capacitor bridge, respectively, and including first and second amplifier outputs;
a first capacitor coupled between the first amplifier input and the first amplifier output; and
a second capacitor coupled between the second amplifier input and the second amplifier output.

5. The integrator circuit of claim 1, further comprising a decimator coupled to first and second integrator outputs and configured to discard one of two successive output samples from the integrator and to provide an output signal corresponding to the one of two successive output samples that was not discarded.

6. The integrator circuit of claim 5, further comprising a second integrator including an input to receive the output signal from the decimator and configured to integrate the output signal from the decimator, the second integrator configured to provide an integrated output signal.

7. The integrator circuit of claim 6, further comprising a quantizer coupled to the second integrator and configured to quantize the integrated output signal to produce a quantized output.

8. The integrator circuit of claim 7, further comprising a feedback loop coupled between an output of the quantizer and the integrator, the feedback loop including an interpolator configured to capture the quantized output once per unit time interval and to output the captured quantized output twice per unit time interval to provide an interpolated feedback signal to the integrator.

9. A method of integrating a measured capacitance, the method comprising:
selectively switching first and second inputs and first and second outputs of a capacitive bridge twice per unit time interval; and
integrating charges on the first and second outputs of the capacitive bridge twice per unit time interval to produce an integrated output signal.

10. The method of claim 9, further comprising decimating the integrated output signal from two samples per unit time interval to one sample per unit time interval to provide a decimated output signal.

11. The method of claim 10, further comprising integrating the decimated output signal to produce an output signal corresponding to a sensed capacitance.

12. The method of claim 11, further comprising:
quantizing the output signal to produce a digital value corresponding to the sensed capacitance; and interpolating the quantized output signal from one sample per unit time interval to two samples per unit time interval to provide an interpolated feedback signal.

13. The method of claim 9, wherein selectively switching the first and second inputs and the first and second outputs of the capacitive bridge comprises:
    selectively coupling the first and second inputs of the capacitive bridge to first and second reference voltages, respectively, and selectively coupling the first and second outputs of the capacitive bridge to first and second input terminals of an integrator, respectively, during a first portion of the unit time interval; and
    selectively coupling the first and second inputs to the second and first reference voltages, respectively, and selectively coupling the first and second outputs to the second and first input terminals of the integrator, respectively, during a second portion of the unit time interval.

14. The method of claim 13, further comprising:
    in the first portion of the unit time interval, selectively coupling a first switched feedback network to the first and second input terminals of the integrator; and
    in the second portion of the unit time interval, selectively coupling a second switched feedback network to the first and second inputs of the integrator.

15. The method of claim 9, further comprising:
    integrating and quantizing a decimated version of the integrated output to produce an output signal; and
    feeding back an interpolated version of the output signal.

16. An integrator circuit comprising:
    a switched capacitor bridge including first and second inputs and first and second outputs, the switched capacitor bridge configured to sample first and second reference voltages twice per unit time interval;
    an integrator including first and second integrator inputs coupled to the first and second outputs of the switched capacitor bridge and including first and second integrator outputs, the integrator configured to sample and integrate charge twice per unit time interval to produce two integrated samples per unit time interval; and
    a circuit coupled to the first integrator and configured to decimate the two integrated samples per unit time interval to produce an output signal representing one integrated sample per unit time interval.

17. The integrator circuit of claim 16, wherein the circuit comprises a second integrator coupled to outputs of the first integrator and configured to integrate charge once per unit time interval to produce the output signal.

18. The integrator circuit of claim 16, wherein the circuit includes one or more additional integrators.

19. The integrator circuit of claim 18, further comprising:
    a quantizer coupled to one of the one or more additional integrators and configured to quantize the integrated output signal to produce a quantized output; and
    a feedback loop coupled to an output of the quantizer, the feedback loop includes an interpolator configured to capture the quantized output once per unit time interval and to output the captured quantized output twice per unit time interval to provide an interpolated feedback signal.

20. The integrator circuit of claim 16, wherein the integrator circuit is used in a delta-sigma converter.

* * * * *